(12) United States Patent
Chang et al.

(10) Patent No.: US 9,663,800 B2
(45) Date of Patent: May 30, 2017

(54) ALKANE EXPORTER AND ITS USE

(71) Applicant: Nanyang Technological University, Singapore (SG)

(72) Inventors: Matthew Wook Chang, Singapore (SG); Binbin Chen, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/409,851

(22) PCT Filed: Jun. 12, 2013

(86) PCT No.: PCT/SG2013/000243
§ 371 (c)(1),
(2) Date: Dec. 19, 2014

(87) PCT Pub. No.: WO2013/191652
PCT Pub. Date: Dec. 27, 2013

(65) Prior Publication Data
US 2015/0184201 A1 Jul. 2, 2015

Related U.S. Application Data

(60) Provisional application No. 61/661,602, filed on Jun. 19, 2012.

(51) Int. Cl.
| | | |
|---|---|---|
| *C12N 1/19* | (2006.01) | |
| *C12P 5/02* | (2006.01) | |
| *C12N 15/31* | (2006.01) | |
| *C07K 14/39* | (2006.01) | |
| *C10L 1/04* | (2006.01) | |
| *C10G 1/00* | (2006.01) | |
| *C07K 14/705* | (2006.01) | |
| *C12N 15/81* | (2006.01) | |

(52) U.S. Cl.
CPC ............... *C12P 5/02* (2013.01); *C07K 14/39* (2013.01); *C07K 14/705* (2013.01); *C10G 1/00* (2013.01); *C10L 1/04* (2013.01); *C12N 15/81* (2013.01)

(58) Field of Classification Search
None
See application file for complete search history.

(56) References Cited

U.S. PATENT DOCUMENTS

2010/0170010 A1 7/2010 Goossens et al.
2011/0214199 A1 9/2011 Coffin

FOREIGN PATENT DOCUMENTS

WO 2010/014631 A2 2/2010

OTHER PUBLICATIONS

Sang, H., Mechanisms of Development 121:1179-1186, 2004.*
Niimi et al., Jpn. J. Infect. Dis. 58:1-7, 2005.*
Ye et al., J. Pediatr. Hematol. Oncol. 33:e120-e121, 2011, abstract only.*
Seret et al., BMC Genomics 10:459, 2009, 11 pages.*
UniProt Accession No. Q6CBB8, May 2011, 2 pages.*
Saier Lab Bioinformatics Group, "3.A.1 The ATP-binding Cassette (ABC) Superfamily", Transporter Classification Database (TCDB), University of California San Diego, 55 pages, obtained from http://www.tcdb.org/search/result.php?tc=3.A.1, last viewed on Mar. 21, 2016.*
Freigassner et al., "Tuning microbial hosts for membrane protein production", Microbial Cell Factories 8:69, 2009, 22 pages.*
Alper et al., "Engineering Yeast Transcription Machinery for Improved Ethanol Tolerance and Production," *Science* 314 (5805):1565-1568, Dec. 8, 2006.
Barth et al., "Physiology and genetics of the dimorphic fungus *Yarrowia lipolytica*," *FEMS Microbiology Reviews* 19:219-237, 1997.
Bauer et al., "Inventory and function of yeast ABC proteins: about sex, stress, pleiotropic drug and heavy metal resistance," *Biochimica et Biophysica Acta* 1461:217-236, 1999.
Beopoulos et al., "*Yarrowia lipolytica*: A model and a tool to understand the mechanisms implicated in lipid accumulation," *Biochimie* 91:692-696, 2009.
Blanchin-Roland et al., "ESCRT-I components of the endocytic machinery are required for Rim101-dependent ambient pH regulation in the yeast *Yarrowia lipolytica*," *Microbiology* 151:3627-3637, 2005.
Borden et al., "Dynamics of Genomic-Library Enrichment and Identification of Solvent Tolerance Genes for *Clostridium acetobutylicum*," *Applied and Environmental Microbiology* 73(9):3061-3068, 2007.
Chen et al., "Transporter engineering for improved tolerance against alkane biofuels in *Saccharomyces cerevisiae*," *Biotechnology for Biofuels* 6:21, 2013, 10 pages.
Conzelmann et al., "A major 125-kd membrane glycoprotein of *Saccharomyces cerevisiae* is attached to the lipid bilayer through an inositol-containing phospholipid," *The EMBO Journal* 7(7):2233-2240, 1988.
de Jong et al., "Systems biology of yeast: enabling technology for development of cell factories for production of advanced biofuels," *Current Opinion in Biotechnology* 23:624-630, 2012.
Dunlop et al., "Engineering microbial biofuel tolerance and export using efflux pumps," *Molecular Systems Biology* 7:487, 2011, 7 pages.
Heckman et al., "Gene splicing and mutagenesis by PCR-driven overlap extension," *Nature Protocols* 2(4):924-932, 2007.
Hou, "Improved Production of Ethanol by Novel Genome Shuffling in *Saccharomyces cerevisiae*," *Appl. Biochem. Biotechnol.* 160:1084-1093, 2010.
Jungwirth et al., "Yeast ABC transporters—A tale of sex, stress, drugs and aging," *FEBS Letters* 580:1131-1138, 2006.
Kalscheuer et al., "Synthesis of Novel Lipids in *Saccharomyces cerevisiae* by Heterologous Expression of an Unspecified Bacterial Acyltransferase," *Applied and Environmental Microbiology* 70(12):7119-7125, Dec. 2004.

(Continued)

*Primary Examiner* — David J Steadman
(74) *Attorney, Agent, or Firm* — Seed IP Law Group LLP

(57) ABSTRACT

Recombinant cell expressing at least one heterologous alkane exporter protein comprising an ATP binding cassette (ABC), wherein the ABC comprises of an amino acid consensus sequence as set forth in SEQ ID No. 1. The use and method of producing or increasing resistance to biofuels with the same.

8 Claims, 5 Drawing Sheets

(56) References Cited

OTHER PUBLICATIONS

Matsushika et al., "Bioethanol Production from Xylose by Recombinant *Saccharomyces cerevisiae* Expressing Xylose Reductase, $NADP^+$-dependent Xylitol Dehydrogenase, and Xylulokinase," *Journal of Bioscience and Bioengineering* 105(3):296-299, 2008.

Mauersberger et al., "Insertional Mutagenesis in the *n*-Alkane-Assimilating Yeast *Yarrowia lipolytica*: Generation of Tagged Mutations in Genes Involved in Hydrophobic Substrate Utilization," *Journal of Bacteriology* 183(17):5102-5109, Sep. 2001.

Nishida et al., "ABC transporters and cell wall proteins involved in organic solvent tolerance in *Saccharomyces cerevisiae*," *Journal of Biotechnology* 165:145-152, 2013.

Riezman et al., "Import of proteins into mitochondria: a 70 kilodalton outer membrane protein with a large carboxy-terminal deletion is still transported to the outer membrane," *The EMBO Journal* 2(12):2161-2168, 1983.

Sheff et al., "Optimized cassettes for fluorescent protein tagging in *Saccharomyces cerevisiae*," *Yeast* 21:661-670, 2004.

Shi et al., "Functional expression and characterization of five wax ester synthases in *Saccharomyces cerevisiae* and their utility for biodiesel production," *Biotechnology for Biofuels* 5:7, 2012, 10 pages.

Stanley et al., "Generation and characterization of stable ethanol-tolerant mutants of *Saccharomyces cerevisiae*," *J. Ind. Microbiol. Biotechnol.* 37:139-149, 2010.

Steen et al., "Metabolic engineering of *Saccharomyces cerevisae* for the production of n-butanol," *Microbial Cell Factors* 7:36, 2008, 8 pages.

Thevenieau et al., "Characterization of *Yarrowia lipolytica* mutants affected in hydrophobic substrate utilization," *Fungal Genetics and Biology* 44:531-542, 2007.

Thevenieau et al., "Uptake and Assimilation of Hydrophobic Substrates by the Oleaginous Yeast *Yarrowia lipolytica*," in Timmins (ed.), *Handbook of Hydrocarbon and Lipid Microbiology*, Springer-Verlag Berlin Heidelberg, 2010, pp. 1514-1527.

YALI0B02544p [Yarrowia lipolytica CLIB122], Dujon et al., "Genome evolution in yeasts," *Nature* 430(6995):35-44, 2004, GenBank Accession No. CAG82646, retrieved from http://ncbi.nlm.nih.gov/protein/CAG82646 on Aug. 13, 2013, 2 pages.

YALI0C20265p [Yarrowia lipolytica CLIB122], Dujon et al., "Genome evolution in yeasts," *Nature* 430(6995):35-44, 2004, GenBank Accession No. CAG82364, retrieved from http://www.ncbi.nlm.nih.gov/protein/CAG82364 on Aug. 13, 2013, 2 pages.

Yu et al., "Synthesis of FAEEs from Glycerol in Engineered *Saccharomyces cerevisiae* Using Endogenously Produced Ethanol by Heterologous Expression of an Unspecific Bacterial Acyltransferase," *Biotechnology and Bioengineering* 109(1):110-115, Jan. 2012.

\* cited by examiner

A

```
                    Walker A
ABC2    835 ERRLLDHVDGFVKPGTLTALMGASGAGKTTLLDVLADRKSTGVVTGEMLVNGEHRDGSFQ
ABC3    837 EKRLLDNVDGWVKPGTLTALMGCSGAGKTTLLDVLADRKATGVITGDMRVNGQKRDASFQ
PDR5    884 TRRILNNVDGWVKPGTLTALMGASGAGKTTLLDCLAERVTMGVITGDILVNGIPRDKSFP
PDR15   899 QRRILNNVDGWVKPGTLTALMGASGAGKTTLLDCLAERVTMGVIAGNIFVDGRLRDESFP ABC2    896 RKTGYVQQQDLHTATATVRESLEFSALLRQPSSIPESEKLAYVDEVIRILEMETYADAVV
ABC3    897 RKTGYVQQQDLHTATSTVREALEFSALLRQPSNVPKAEKIAYVDEVIDILEMQAYADAVV
PDR5    944 RSIGYCQQQDLHLKTATVRESLRFSAYLRQPAEVSIEEKNRYVEEVIKILEMEKYADAVV
PDR15   959 RSIGYCQQQDLHLKTATVRESLRFSACLRQPSSVSIEEKNRYVEEVIKILEMQQYSDAVV
                C-loop                           Walker B
ABC2    956 GVPGEGLNVEQRKRLTIGVELAAKPELLLFLDEPTSGLDSQTAWSIVKLLKKLAANGQAI
ABC3    957 GVPGEGLNVEQRKRLTIGVELAAKPELLLFLDEPTSGLDSQTAWSIICLLKKLANRGQAI
PDR5    1004 GVAGEGLNVEQRKRLTIGVELTAKPKLLVFLDEPTSGLDSQTAWSICQLMKKLANHGQAI
PDR15   1019 GVAGEGLNVEQRKRLTIGVELAARPKLLVFLDEPTSGLDSQTAWDTCQLMRKLATHGQAI
         H-loop
ABC2    1016 LCTIHQPSAILFQEFDRLLFLASGGRTVYYGDIGPOSSILTEYFERNGADPCPKQGNPAE
ABC3    1017 LCTIHQPSAILFQEFDRLLFMTLGGKTVYYGDIGANSSALINYFESKGADPCPEEANPAE
PDR5    1064 LCTIHQPSAILMQEFDRLLFMQRGGKTVYFGDLGEGCKTMIDYFESHGAHKCPADANPAE
PDR15   1079 LCTIHQPSAILMQQFDRLLFLQKGGQTVYFGDLGEGCKTMIDYFESKGAHKCPPDANPAE
```

B

| | Without alkane | Decane | Undecane |
|---|---|---|---|
| ABC2-E988Q | ● ● ● | | |
| ABC2-H1020A | ● ● ● | | ● ● |
| ABC3-E989Q | ● ● ● | | |
| ABC3-H1021A | ● ● ● | | ● |

Figure 5

ALKANE EXPORTER AND ITS USE

CROSS-REFERENCE TO RELATED APPLICATION

This application claims the benefit of priority of U.S. Provisional Patent Application No. 61/661,602 filed Jun. 19, 2012, the contents of which being hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148.471USPC_SEQUENCE_LISTING.txt. The text file is 42 KB, was created on Nov. 16, 2015, and is being submitted electronically via EFS-Web.

FIELD OF THE INVENTION

Yeast recombinant systems having improved Alkane tolerance.

BACKGROUND OF THE INVENTION

The development of renewable biofuels, such as bioethanol [1], butanol [2], bio-diesel [3-5] and jetfuels [6], helps to address energy security and climate change concerns. For economically industrial production of biofuels, titers and yield of biofuels synthesis must be sufficiently high. However biofuels are frequently toxic to cells, thereby placing a limit on the yield. Hence, biofuel toxicity is an important issue that needs to be addressed. There are several strategies for addressing biofuel toxicity in microorganisms. Alper et al. [7] employed a global transcription machinery engineering (gTME) approach to improve ethanol tolerance. Stanley et al. [8] used an adaptive evolution engineering method to select stable ethanol tolerant mutants of *Saccharomyces cerevisiae*, whereas Hou et al. [9] developed novel genome shuffling method to improve biofuel tolerance.

ATP binding cassette transporters (ABC transporters) are transmembrane ion channels found in all organisms. ABC transporters often share common domain architecture with two transmembrane domains (TMD) and two nucleotide binding domains (NBD) that hydrolise ATP or other nucleotides. Pleitropic drug resistance 5 (PDR5) is the most extensively studied ABC transporter from *S. cerevisiae*.

*Yarrowia lipolytica*, a non-conventional oleaginous yeast that efficiently assimilates and utilizes hydrophobic substrates such as alkanes, fatty acids and lipids, was recently used as a model system to study mechanisms of assimilation and degradation of hydrophobic substrates (HS) [12-14]. The characterization of *Y. lipolytica* mutant, ΔABC1 (YALI0E14729g), with a defective phenotype for hexadecane (C16) utilization, suggested that ABC1 may be involved in import or export of long chain alkanes [15]. Similarly, *Y. lipolytica* mutant ΔABC2 (YALI0C20265g) showed a decreased cell growth on decane [16]. In addition, genome exploration revealed two homologues, ABC3 (YALIB02544g) and ABC4 (YALIB012980g), which may be also involved in alkane transportation.

Toward the aim of improving alkane tolerance in yeast, classical strain engineering strategies, including mutagenesis and adaptive evolutionary engineering together with genome shuffling and genomic library [17], have been widely used. However, it takes about 6 months to generate ethanol-tolerant mutant by employing the adaptive evolutionary engineering method [8]. Some strategies, are extremely laborious to generate positive mutants. For example, the procedure of yeast genome shuffling, includes EMS treatment, sporulation, spore purification, adequate cross and mutant selection [9]. In addition, for the genomic library approach, more than 10,000 transformants have to form genomic library [17] and be screened. Further, this approach has little room for errors as it needs very high ligation and transformation efficiency. It would require personnel with very good molecular biology techniques. For improvement strategies, such as the random mutagenesis and selection, there is no guarantee about the positive mutant being effective and stable.

SUMMARY

A first aspect of the invention includes a recombinant cell expressing at least one heterologous alkane exporter protein comprising an ATP binding cassette (ABC), wherein the ABC comprises of an amino acid consensus sequence as set forth in SEQ ID No. 1.

A further aspect of the invention includes the use of the recombinant cell for biofuel production.

Another aspect of the invention includes a method for the production of a biofuel comprising cultivating the recombinant cell under conditions that allow (i) the expression of the at least one heterologous alkane exporter protein; and (ii) the production of a biofuel.

Another aspect of the invention includes a method of increasing resistance towards biofuel toxicity in a cell comprising: (a) introducing a nucleic acid molecule encoding for a heterologous alkane exporter protein comprising an ATP binding cassette (ABC), wherein the ABC comprises or consists of an amino acid consensus sequence as set forth in SEQ ID No. 1; and (b) cultivating the cell under conditions that allow expression of the heterologous alkane exporter protein.

Other aspects of the invention would be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following drawings.

FIG. 5. Transporter sequence comparison and alkane susceptibility assay of ABC2 and ABC3 mutants. (A) Multiple sequence alignment of NBD2 of ABC transporters. ABC2 [GenBank: CAG82364] (SEQ ID NO: 6); ABC3 [GenBank: CAG82646] (SEQ ID NO: 7); PDR5 [GenBank: CAA99359] (SEQ ID NO: 8); and PDR15 [GenBank: AAB64846] (SEQ ID NO: 9). Starting amino acid numbers are shown in each line. Sequences were aligned in ClustalW, and the shading was created by Mobyle Pasteur Boxshade. Single letter abbreviations for amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr. (B) Alkane susceptibility assay with ABC2 and ABC3 mutants.

DETAILED DESCRIPTION

Figure 1:
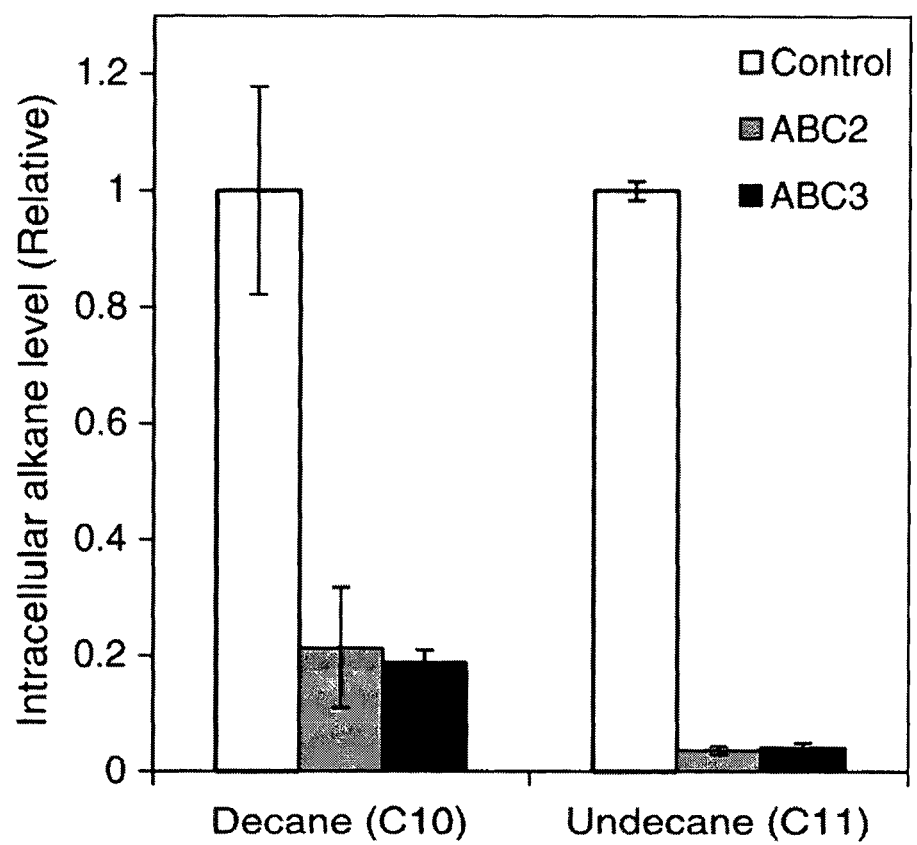
FIG. 1. Intracellular alkane accumulation by ABC2 and ABC3. *S. cerevisiae* BY4741 with and without ABC2/3 were cultured under exposure of 0.5% alkane or 20% undecane. After 48 h incubation, intracellular alkane levels were measured. Intracellular alkane levels were normalized to that of control carrying empty plasmid. Data shown are the mean±SD of four biological replicates.

We focused on harnessing pleiotropic drug resistance (PDR) family of the ATP-binding cassette (ABC) in yeast, as a direct mechanism for reducing biofuel toxicity.

Accordingly, a first aspect of the invention comprises a recombinant cell expressing at least one heterologous alkane exporter protein comprising an ATP binding cassette (ABC), wherein the ABC comprises of an amino acid consensus sequence as set forth in SEQ ID No. 1.

The ATP binding cassette (ABC) includes a nucleotide binding domain of the ABC wherein the nucleotide binding domain (NBD) of the ABC comprises or consists of a amino acid consensus sequence set forth in SEQ ID No. 1. The NBD of both ABC2 as set forth in SEQ ID No. 2, and ABC3 as set forth in SEQ ID No. 3 are examples of NBD having the amino acid consensus sequence set forth in SEQ ID No. 1.

The recombinant cell includes an expression system. The expression system as used herein, refers to a modified operon the addition or modification of a nucleic acid sequence needed for gene sequence expression. The construct may include promoters and or enhancers as known in the art. Promoter regions vary from organism to organism, but are well known to persons skilled in the art for different organisms. The nucleic acid expression system can be synthesised de novo for protein expression of alkane exporter comprising an ATP binding cassette (ABC) in a cell or made by any means known in the art.

The term 'heterologous' refers to a nucleic acid sequence expressing a protein whereby the nucleic acid sequence is derived from a different organism often the sequence was initially cloned from or derived from a different cell type or a different species from the recipient. Typically the genetic material coding for the protein (the nucleic acid such as complementary DNA) is added to the recipient cell. The genetic material that is transferred typically must be within a format that encourages the recipient cell to express the the nucleic acid as a protein. Suitable expression systems are known in the art.

The term "nucleic acid" as used herein refers to any isolated or synthesised nucleic acid molecule in any possible configuration, such as single stranded, double stranded or a combination thereof. Isolated nucleic acids include for instance DNA molecules, RNA molecules, analogues of the DNA or RNA generated using nucleotide analogues or using nucleic acid chemistry, locked nucleic acid molecules (LNA), peptide nucleic acid molecules (PNA) and tecto-RNA molecules. DNA or RNA may be of genomic or synthetic origin and may be single or double stranded. Such nucleic acid can be e.g. mRNA, cRNA, synthetic RNA, genomic DNA, cDNA, synthetic DNA, a copolymer of DNA and RNA, oligonucleotides, etc. Any nucleic acid capable of expressing the polypeptides of the invention including the nucleotide binding domain of the ABC having an amino acid consensus sequence set forth in SEQ ID No. 1, including ABC2 or ABC3 as set forth in SEQ ID NO. 4 and SEQ ID NO. 5 respectively in a cell would be suitable. Preferably the nucleic acid molecule encoding the heterologous alkane exporter protein comprising an ATP binding cassette (ABC) construct.

In one embodiment the expression system is comprised in a vector.

The term "vector" relates to a single or double-stranded circular nucleic acid molecule that can be transfected into cells and replicated within or independently of a cell genome. A circular double-stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding an alkane exporter comprising an ATP binding cassette (ABC) can be inserted into a vector by cutting the vector with restriction enzymes and ligating the pieces together. Preferably the vector is a plasmid The term 'alkane exporter protein comprising amino acid sequence expressing an ATP binding cassette (ABC)' capable of exporting alkanes. Preferably the alkane exporter protein relates to an ABC transporter that allows cells to survive in at least 0.75% alkane. Preferably the alkane exporter protein is capable of exporting C6-C16 alkanes, preferably C8-C12 alkanes, more preferably C10-C11 alkanes. In various embodiments the expression of the ABC transporter allows cells to survive in at least 0.75% decane or to survive in 20% undecane. Further, an alkane exporter relates to an ABC transporter that is able to reduce the intracellular alkane level by at least 5 fold when cells are exposed to between 0.5% to 20% alkane compared to cells not expressing the ABC transporter. In various embodiments the expression of the ABC transporter allows cells to reduce the intracellular alkane level by at least 5 fold when cells are exposed to between 0.5% decane or to reduce the intracellular alkane level by at least 30 fold when cells are exposed to between 20% undecane compared to cells not expressing the ABC transporter.

In some embodiments the nucleotide binding domain comprises amino acid sequence set forth in SEQ ID No. 2. In such embodiments preferably the ABC comprises amino acid sequence set forth in SEQ ID No. 4.

In other embodiments the nucleotide binding domain comprises amino acid sequence set forth in SEQ ID No. 3. In such embodiments preferably the ABC comprises amino acid sequence set forth in SEQ ID No. 5.

Preferably the expression system is a cell based expression system. In some embodiments the cell is a eukaryotic cell. Preferably, the cell is a yeast cell. Preferably, the cell is of the genus *Saccharomyces*. Most preferably the cell is a *Saccharomyces cerevisiae* cell.

Another aspect of the invention includes the use of the recombinant cell for biofuel production. Preferably the biofuel comprises or consists of C6-C16 alkanes.

Another aspect of the invention includes a method for the production of a biofuel comprising cultivating the recombinant cell under conditions that allow (i) the expression of the at least one heterologous alkane exporter protein; and (ii) the production of a biofuel.

In some embodiments the production of biofuel may be achieved by reducing alkane accumulation in a cell Another aspect of the invention includes a method of increasing resistance towards biofuel toxicity in a cell comprising: (a) introducing a nucleic acid molecule encoding for a heterologous alkane exporter protein comprising an ATP binding cassette (ABC), wherein the ABC comprises of an amino acid consensus sequence as set forth in SEQ ID No. 1; and (b) cultivating the cell under conditions that allow expression of the heterologous alkane exporter protein.

Preparing a recombinant cell may comprise the steps of: constructing an expression system capable of expressing an alkane exporter comprising an ATP binding cassette (ABC) wherein a nucleotide binding domain (NBD) of the ABC comprises or consists of a amino acid consensus sequence set forth in SEQ ID No. 1; and introducing the construct to the cell.

In various embodiments the expression system is a vector preferably a plasmid as discussed herein for use in the cell.

In some embodiments the recombinant cell comprises an expression system constructed with the nucleotide binding domain (NBD) comprising or consisting of an amino acid consensus sequence set forth in SEQ ID No. 1. In various embodiments the NBD sequence is set forth in SEQ ID No. 2. In such embodiments preferably the ABC comprises amino acid sequence set forth in SEQ ID No. 4.

In other embodiments the recombinant cell comprises an expression system constructed with the nucleotide binding domain (NBD) comprising or consisting of an amino acid consensus sequence set forth in SEQ ID No. 1. In various embodiments the NBD sequence is set forth in SEQ ID No. 3. In such embodiments preferably the ABC comprises amino acid sequence set forth in SEQ ID No. 5.

In some embodiments the cell is a eukaryotic cell. Preferably, the cell is a yeast cell. Preferably, the cell is of the genus *Saccharomyces*. Most preferably the cell is a *Saccharomyces cerevisiae* cell.

Preferably biofuel refers to an alkane. Preferably the biofuel is a C6-C16 alkane, preferably C8-C12 alkane, more preferably C10-C11 alkanes. Alkane may refers to a medium length alkane of C6, C7, C8, C9, C10, C11, C12. In various embodiments alkane refers to a decane. In various embodiments alkane refers to an undecane.

EXAMPLES

To determine the potential of ACB transporter as alkane exporters, we screened *Y. lipolytica* ABC1, ABC2, ABC3 and ABC4 for their transport potential, and have selected ABC2 and ABC3 as our candidates. By heterologous expression of ABC2 and ABC3 in *S. cerevisiae*, the tolerance of Baker's yeast against decane and undecane has been significantly improved.

Hitherto, there has been no reported characterization of ABC2 and ABC3 transporters of *Y. lipolytica* in other organisms. With the expression of ABC2 and ABC3 in *S. cerevisiae*. (FIG. 1), cells expressing ABC2 and ABC3 had ~5-fold lower intracellular decane level relative to the control. Further, ABC2 and ABC3 transporters were shown to reduce the intracellular undecane level approximately 30-fold compared to the control sample. The sharp decrease in intracellular alkane levels strongly suggests that ABC2 and ABC3 may function as decane and undecane exporters.

Most notably, this is the first study to characterize the function of ABC2 and ABC3 transporters, and these two transporters are the first characterized eukaryotic medium-chain alkane exporters.

Better Strategy Over Other Methods

Compared with classical tolerance improvement strategies, our use of heterologous expression of transporters has the following distinct advantages:

a) It is less time consuming to generate tolerance strains through heterologous expression of transporters, as compared to conventional evolutionary strategies. For example, it takes about 6 months to generate ethanol-tolerant mutant by employing the adaptive evolutionary engineering method [8]. For the heterologous expression of ABC2 and ABC3, it takes less than 3 days to express these transporters in host cells to increase cell tolerance.

b) Our strategy requires significantly less effort to carry out. The process of heterologous expression of transporters involves only 2 simple techniques, namely transformation and induction.

c) Our approach has a stronger guarantee for performance. Our heterologous transporters have been confirmed to improve cell tolerance once they are expressed.

For Yield Improvement in Biofuel Production

In the process of biofuel production such as alkane, product toxicity is the chief concern and it lowers the yield and titers significantly. To overcome this shortcoming, we have demonstrated that heterologous expression of ABC2 and ABC3 can increase the tolerance of *S. cerevisiae* against decane and undecane. And several studies show improvement in tolerance leads to clear increases in biofuel yield. For example, ethanol production in an engineered strain of *S. cerevisiae* was improved by 15% when its ethanol and glucose tolerance were improved through global transcriptional machinery engineering [7]. Limonene tolerance in *E. coli* was improved by heterologously expressing an efflux pump and the corresponding strain showed a 64% improvement in limonene yield [18]. Thus, there is clear evidence that tolerance improvements can increase production. And we believe that the improvement of C10 and C11 alkane tolerance of *S. cerevisiae* can enhance the possible alkane yield.

Strains and Media

All cells involved in cloning experiments were *E. coli* TOP10 (Invitrogen) unless otherwise stated. Luria-Bertani (BD) was used as the medium for cloning studies unless otherwise stated. Ampicillin (100 μg/ml) was added to the culture media for antibiotic selection where appropriate.

The yeast strains *S. cerevisiae* BY4741 (ATCC 201388) and *Y. lipolytica* CLIB122 (CIRM) were used for function characterization. *S. cerevisiae* BY4741 were cultured in rich medium (YPD), synthetic minimal medium lacking uracil (SC-U) or induction medium. YPD medium (1% yeast extract, 2% peptone, 2% glucose) was used to routinely maintain wild type strain. SC-U medium (0.67% yeast nitrogen base, 0.192% uracil dropout and 2% raffinose) was used for growing pYES2 transformants. Induction medium (0.67% yeast nitrogen base, 0.192% uracil dropout, 1% raffinose and 2% galactose) was used for protein induction in *S. cerevisiae* cells. Medium containing 0.67% yeast nitrogen base supplemented with 0.5% casein hydrolysate and 2% glucose was used for growth of *Y. lipolytica* for qRT-PCR sample preparation. Yeast growth media components were purchased from Sigma-Aldrich.

Alkanes (octane (C8), nonane (C9), decane (C10), undecane (C11) and dodecane (C12)) purchased from Sigma-Aldrich were added to culture medium for protein function analysis where appropriate.

Plasmid Construction

Plasmid pYES2 (Invitrogen) with the GAL1 promoter was used as an expression vector. To clone 6×His-tagged ABC2, genomic DNA of *Y. lipolytica* CLIB122 was used as a PCR template with two pairs of primers ABC2-F1, ABC2-R1 and ABC2-F2, ABC2-R2. The two PCR products were combined through the Splicing Overlap Extension (SOE) method [19] using primers ABC2-F1 and ABC2-R2. The resulting DNA fragment was digested with Hind III and Not I and cloned into pYES2 cut with the same restriction enzymes, creating pYES2ABC2. Plasmid pYES2ABC3 was constructed as for pYES2ABC2. Site-directed mutagenesis of transporters, ABC2-E988Q, ABC2-H1020A, ABC3-E989Q and ABC3-H1021A were constructed by mutating glutamate to glutamine and histidine to alanine respectively.

Plasmid pYES2ABC2-EGFP, which encodes yeast enhanced green fluorescent protein (EGFP) at the C-terminus of the ABC2 open reading frame, was constructed as follows. We used pYES2ABC2 as a PCR template with primer set ABC2-F1 and ABC2-EGFP-R2. The resulting DNA fragment was digested with Hind III and Not I and cloned into pYES2 cut with the same restriction enzymes, creating pYES2ABC2-1. EGFP was amplified from pKT127 (Euroscarf) [20] using primer sets EGFP-F and EGFP-R, digested with Not I and Sph I and inserted into the same restriction sites of pYES2ABC2-1 to create pYES2ABC2-EGFP. Plasmid pYES2ABC3-EGFP was constructed as for pYES2ABC2-EGFP. For construction of pYES2EGFP, EGFP was amplified by PCR from pKT127 using primers EGFP-control-F and EGFP-R, digested with Not I and Sph I and cloned into pYES2. All restriction and ligation enzymes were purchased from New England Biolabs (NEB).

Quantitative RT-PCR

To assess whether ABC1, ABC2, ABC3 and ABC4 are involved in alkane transport in *Y. lipolytica*, we analysed the effects of alkanes with different chain length (C8-C12) on the transcription levels of these four ABC transporter genes using quantitative RT-PCR.

Total RNA samples from 24 h alkane treated and untreated *Y. lipolytica* CLIB122 cells were prepared using RNeasy Mini Kit (Qiagen), followed by cDNA synthesis using H minus Reverse transcriptase kit (Fermentas). Quantitative RT-PCR analysis was performed on a Bio-Rad iQ5 real-time PCR detection system using SsoFast EvaGreen Supermix kit (Bio-Rad). The actin gene (YALI0D08272g) [21] was used as reference gene for *Y. lipolytica*. Relative mRNA levels were derived using comparative $C_T$ method.

Figure 3:
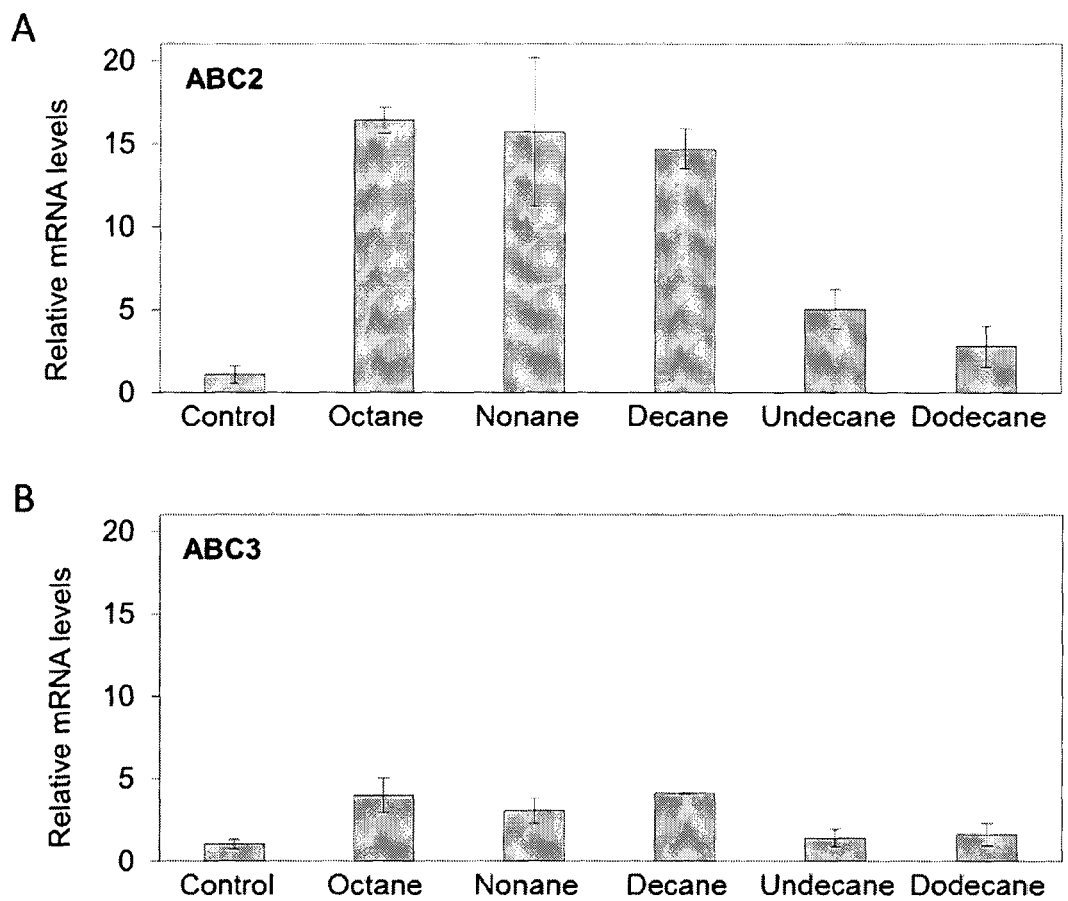
FIG. 3. mRNA transcripts levels of ABC2 and ABC3 in *Y. lipolytica*. Quantitative RT-PCR analysis of ABC2 (A) and ABC3 (B) in *Y. lipolytica* cells corresponding to treatment with octane, nonane, decane, undecane and dodecane (C8-C12). Each value of qRT-PCR was normalized to β-actin expression levels and expressed as the fold change relative to the levels detected in control samples, which were cells without alkane treatment and set equal to 1. Error bars represent the SD of triplicate.

Compared with control samples without alkane treatment, the transcription levels of ABC1 and ABC4 did not change much when treated with different alkanes (C8-C12) (data not shown). However, the mRNA levels of ABC2 were significantly increased when *Y. lipolytica* was treated with octane (C8), nonane (C9), decane (C10) and undecane (C11) ($p<0.05$), while the mRNA levels of ABC3 were significantly increased toward nonane (C9) and decane (C10) ($p<0.05$) (FIG. 3). These results strongly suggest that two of the ABC transporters, ABC2 and ABC3, may play a critical role in the transport of alkanes with shorter chain length (C8, C9, and C10). Thus, based on the qRT-PCR results, ABC2 and ABC3 were chosen for further analysis of their alkane transport behaviour.

Expression and Subcellular Localization of ABC2 and ABC3

Western Blot Analysis

To confirm the expression of these two transporters, a 6×His tag was attached to the C terminus of ABC2 and ABC3.

*S. cerevisiae* cells carrying the plasmids encoding the 6×His-tagged ABC2 and ABC3 were cultured in induction medium and harvested at OD600=1-2 (early exponential phase). The protein extraction method here is based on alkaline lysis [22] and glass bead lysis [23] methods. The following handling process was carried out in the cold room (~4° C.). Cell pellets (around 14 mg) were resuspended in 300 μl cold lysis buffer (0.1 M NaOH, 2% β-mercaptoethanol, and protease inhibitor mixture (Roche Applied Science)). After 5 min, glass beads (425-600 μm, Sigma) were added to the suspension until the suspension was covered. Cells were lysed by vortexing for 2 min. The lysate obtained was clarified by transferring supernatant into a new tube. Protein in the lysate was fully dissolved by adding SDS (final concentration around 2%) and gently stirring for 10 min. After centrifugation, the supernatant was mixed equally with Laemmli sample buffer (Bio-Rad) and separated on a SDS-polyacrylamide gel. The sample gels were used for blotting. Proteins were blotted onto a 0.2 μm nitrocellulose membrane (Bio-Rad) through Trans-Blot Turbo Blotting System (Bio-Rad). 6×His-tagged ABC2 and ABC3 were detected using anti-6×His-tag antibody (HRP) (ab1187, Abcam) and 3,3',5,5'-Tetramethylbenzidine (TMB) Liquid Substrate (Sigma) system.

Figure 4:
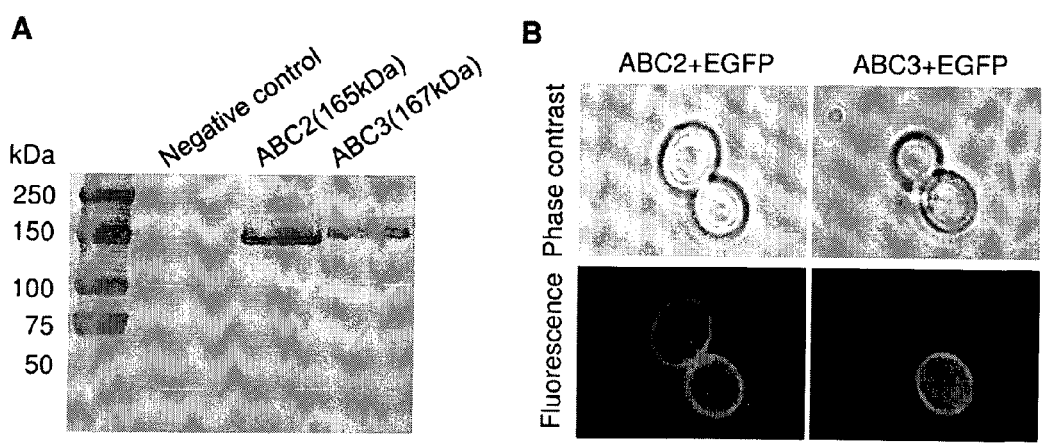
FIG. 4. Expression and subcellular localization of ABC2 and ABC3. (A) Expression of ABC2 and ABC3. The expression of ABC2/3 carrying 6×His tag were confirmed by western blot analysis. The arrow shows the right band size. The positions of molecular mass markers are indicated at left. (B) Subcellular localization of ABC2 and ABC3 determined by fluorescence microscopy. Yeast cells carrying plasmid encoding ABC2/3-EGFP fusion proteins were cultured and harvested. Phase contrast figures and fluorescence figures are shown.

Through immunodetection for 6×His-tagged proteins, specific bands could be assigned to ABC2 (165 kDa) and ABC3 (167 kDa) (FIG. 4A). This western blot results confirm the expression of ABC2 and ABC3.

Fluorescence Microscopy

Next, to further analyse the localization of ABC2 and ABC3, each of them was tagged with EGFP at its C terminus.

*S. cerevisiae* BY4741 cells carrying plasmid pYES2ABC2-EGFP and pYES2ABC3-EGFP were grown to the early logarithmic phase in induction medium, harvested and mounted on the poly-L-lysine-coated slide glass. EGFP fluorescence was analysed with a fluorescent microscope (Zeiss Axio Scope A1).

As shown in FIG. 4B, strong fluorescence was observed on the plasma membrane of cells containing ABC2-EGFP and ABC3-EGFP fusion proteins respectively. These results suggest that ABC2 and ABC3 are located on the plasma membrane of *S. cerevisiae* cells.

Toxicity Test
Alkane Susceptibility Test on Agar Plate

Alkane susceptibility test on plates was performed according to the methods of Mauersberger et al. [14, 15]. Exponentially growing cells in induction medium were centrifuged and re-suspended with induction medium at OD600=1. Ten microliter aliquots of successive 10-fold dilutions (non diluted, 10-1, 10-2, 10-3) of cells were spotted onto the induction medium plate. Medium chain alkanes were supplied as vapour phase by placing 200 μl alkane on a sterile filter paper in the lid of the petri dish. Plates were incubated at 28° C. for 2 days.

Alkane Susceptibility Test in Liquid Culture

Overnight culture was diluted into 5 ml induction medium in 50 ml glass bottle (Sigma) at an initial $OD_{600}$ of 0.4. Alkanes were added as different final concentration. Bottles were sealed tightly with butyl rubber stopper (Sigma) and silver aluminum seal (Sigma). Liquid culture was performed at 28° C. with shaking. Growth was monitored by measuring the $OD_{600}$ at different time point. Cell culture used for time point OD checking was collected from the glass bottle using needle and syringe.

Viability Improvement Over Native *S. cerevisiae*

Toxicity test was implemented to study the effect of ABC2 and ABC3 on the tolerance of the cells toward alkanes. The toxic effects of alkanes on *S. cerevisiae* with ABC2 and ABC3 were measured through alkane susceptibility test on agar plates. FIG. 2A shows that for cells expressing ABC2 and ABC3, the cell tolerance toward decane and undecane was considerably improved. It was observed that the expression of ABC2 would lead higher tolerance toward decane than ABC3.

To further analyze the effect of ABC2 and ABC3 toward decane and undecane, alkane susceptibility tests in liquid culture were conducted. As shown in FIG. 2B, 0.5% decane and 20% undecane would cause a significant decrease in viability of the control cells. With the expression of ABC2, decane tolerance was boosted about 80-fold (20% vs. 0.25% decane) and cells can survive in 20% undecane. For ABC3, decane tolerance is increased slightly by about 3-fold (0.75% vs. 0.25% decane) and cells are resistant to 20% undecane. It is apparent that the expression of ABC2 and ABC3 transporters improved the tolerance toward C10 and C11 alkanes.

The results on agar plates and in liquid medium showed that both ABC2 and ABC3 expressing cells have greatly enhanced tolerance toward decane and undecane compared with native *S. cerevisiae*.

Gas Chromatography (GC) Analysis

Intracellular alkane accumulation was analysed with GC-FID after 48 h incubation with 0.5% decane or 20% undecane.

After induction for 48 h with or without addition of alkanes, *S. cerevisiae* cells transformed with pYES2, pYES2ABC2 and pYES2ABC3 were harvested at 6000 g for 5 min at 4° C. After washing with 50 mM Tris.Cl, cells were equally divided into two parts, one part for alkane GC analysis and the other for determination of total protein concentration. For GC analysis, cell pellets were re-suspended in freshly prepared Chloroform/Methanol (v/v, 2:1). Dodecane was added into cell suspension as an internal standard. Acid-washed glass beads were added until the suspension was covered. Cells were then lysed by mechanical agitation using FastPrep-24 (MPBio) for 6 min at 6 m/s. The crude extract was obtained by pipette. After addition of autoclaved ddH2O, the crude extract was emulsified for 10 min by inversion. After centrifuge, the crude extract was separated into two phases. The bottom phase containing alkane was transferred into a new 1.5 ml microcentrifuge tube and purified as above with HPLC grade chloroform and autoclaved ddH2O until particulate matter was no longer observable. The purified solution was transferred into a clear GC vial for GC analysis. To check the total protein concentration, Cell pellets were re-suspended into 50 mM Tris.Cl and lysed via mechanical agitation with acid-washed glass beads using FastPrep-24 for 6 min at 6 m/s. Protein concentration of obtained crude extract was determined using the Bradford protein assay (Bio-Rad). Intracellular alkane levels were normalized to internal standard and cell lysate protein content.

Novel Use of ABC2 and ABC3 for Tolerance Improvement in *S. cerevisiae* Toward Decane and Undecane After confirming the function of ABC2 and ABC3 transporters, which can pump out decane and undecane out of cell, we demonstrated that the expression of ABC2 and ABC3 increased *S. cerevisiae* tolerance toward decane and undecane through lowering intracellular alkane level.

Figure 2:
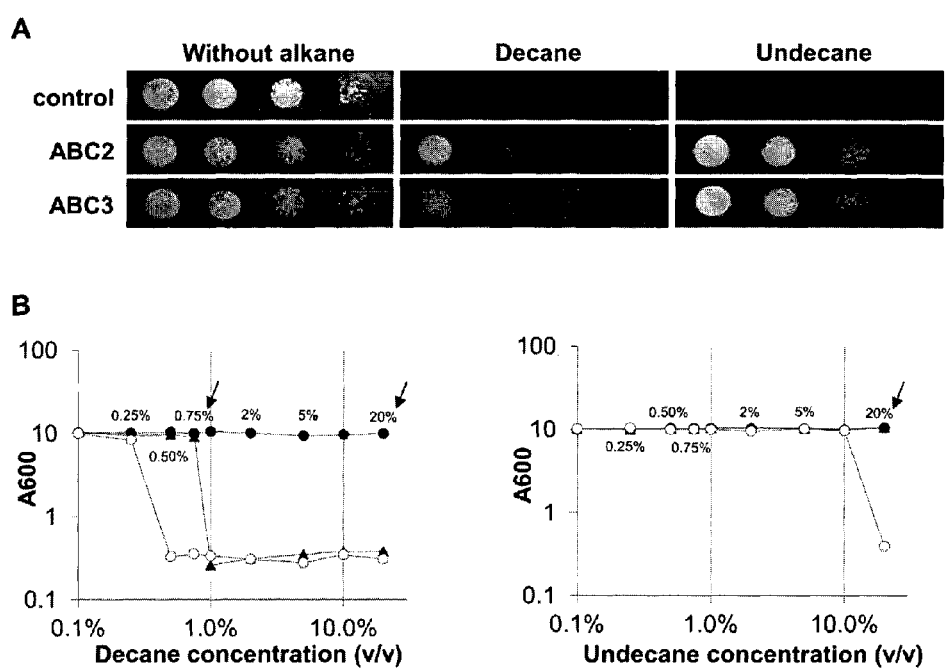
FIG. 2. Alkane susceptibility test for *S. cerevisiae*. The alkane susceptibility was tested in cells expressing ABC2/3 or with empty plasmid. (A) Alkane susceptibility test on agar plate. Serial dilutions of cells expressing ABC2/3 were spotted on agar plates with alkanes (decane, undecane) as vapour phase. Plates were incubated at 28° C. for 2 days. (B) Alkane susceptibility test in liquid culture. Overnight cell culture was diluted into induction medium (final OD600=0.4) with different alkanes (decane & undecane) concentrations. The plates were incubated for 48 hr at 28° C. The OD600 value of each sample was determined and plotted against its corresponding alkane concentration. Symbols for strains are: control sample with empty plasmid (open circle), cells expressing ABC2 (filled circle), cell expressing ABC3 (filled triangle).

Proved by the toxicity test, as shown in FIG. 2, we found that both ABC2 and ABC3 expressing cells exhibited enhanced tolerance toward decane and undecane. This is the first report demonstrating that the expression of ABC2 and ABC3 transporters improves the cell tolerance toward decane and undecane.

Glutamate is Required for Energy-Dependent Efflux Pumping of ABC2 and ABC3

Two different models of ATP hydrolysis mechanisms were proposed for ABC transporters before: the "catalytic carboxylate" model and the "catalytic dyad" model. According to the "catalytic carboxylate" model, the highly conserved glutamate residue at the C terminus of the Walker B motif is essential for ATP hydrolysis. However, in the "catalytic dyad" model, interactions between glutamate of the Walker B motif and the histidine of the H-loop are a prerequisite for ATP hydrolysis.

Sequence alignment of ABC2, ABC3, pleitropic drug resistance 5 (PDR5) and pleitropic drug resistance 15 (PDR15), of the pleitropic drug resistance network in yeast, showed that these proteins have high similarities in NBD domains which include Walker A motif, Walker B motif, C-loop and H-loop (FIG. 5A). Similar to the widely studied PDR5 model, critical amino acids such as glutamate in C-terminus of Walker B motif and histidine of H-loop are only present in NBD2 but not in NBD1 for ABC2 and ABC3. Hence, to determine the ATP hydrolysis mechanism of ABC2 and ABC3, the glutamate (E988 for ABC2 and E989 for ABC3) and the histidine (H1020 for ABC2 and H1021 for ABC3) in NBD2 of ABC2 and ABC3 were mutated to glutamine and alanine, respectively. As shown in FIG. 5B, ABC2-E988Q and ABC3-E989Q mutants were highly sensitive against both decane and undecane, while ABC2-H1020A and ABC3-H1021A mutants still showed increased tolerance against undecane and decreased resistance against decane. Therefore, histidine is deemed not as essential as glutamate for these transporters' activity, and ATP is most likely to be hydrolyzed by the catalytic carboxylate mechanism.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numberical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

REFERENCES

[1] A. Matsushika, S. Watanabe, T. Kodaki, K. Makino, and S. Sawayama, "Bioethanol production from xylose by recombinant *Saccharomyces cerevisiae* expressing xylose reductase, NADP(+)-dependent xylitol dehydrogenase, and xylulokinase," Journal of bioscience and bioengineering, vol. 105, pp. 296-9, March 2008.

[2] E. J. Steen, R. Chan, N. Prasad, S. Myers, C. J. Petzold, A. Redding, M. Ouellet, and J. D. Keasling, "Metabolic engineering of *Saccharomyces cerevisiae* for the production of n-butanol," Microbial cell factories, vol. 7, p. 36, 2008.

[3] R. Kalscheuer, H. Luftmann, and A. Steinbuchel, "Synthesis of Novel Lipids in *Saccharomyces cerevisiae* by Heterologous Expression of an Unspecific Bacterial Acyltransferase," Applied and Environmental Microbiology, vol. 70, pp. 7119-7125, 2004.

[4] K. O. Yu, J. Jung, S. W. Kim, C. H. Park, and S. O. Han, "Synthesis of FAEEs from glycerol in engineered *Saccharomyces cerevisiae* using endogenously produced ethanol by heterologous expression of an unspecific bacterial acyltransferase," Biotechnology and bioengineering, vol. 109, pp. 110-5, January 2012.

[5] S. Shi, J. Octavio Valle-Rodriguez, S. Khoomrung, V. Siewers, and J. Nielsen, "Functional expression and characterization of five wax ester synthases in *Saccharomyces cerevisiae* and their utility for biodiesel production," Biotechnology for Biofuels, vol. 5, p. 7, 2012.

[6] B. de Jong, V. Siewers, and J. Nielsen, "Systems biology of yeast: enabling technology for development of cell factories for production of advanced biofuels," Current opinion in biotechnology, Dec. 12, 2011.

[7] H. Alper, J. Moxley, E. Nevoigt, G. R. Fink, and G. Stephanopoulos, "Engineering yeast transcription machinery for improved ethanol tolerance and production," Science, vol. 314, pp. 1565-8, Dec. 8, 2006.

[8] D. Stanley, S. Fraser, P. J. Chambers, P. Rogers, and G. A. Stanley, "Generation and characterisation of stable ethanol-tolerant mutants of *Saccharomyces cerevisiae*," Journal of industrial microbiology & biotechnology, vol. 37, pp. 139-49, February 2010.

[9] L. Hou, "Improved production of ethanol by novel genome shuffling in *Saccharomyces cerevisiae*," Applied biochemistry and biotechnology, vol. 160, pp. 1084-93, February 2010.

[10] H. Jungwirth and K. Kuchler, "Yeast ABC transporters—A tale of sex, stress, drugs and aging," FEBS Letters, vol. 580, pp. 1131-1138, 2006.

[11] B. E. Bauer, H. Wolfger, and K. Kuchler, "Inventory and function of yeast ABC proteins: about sex, stress, pleiotropic drug and heavy metal resistance," Biochimica et Biophysica Acta (BBA)—Biomembranes, vol. 1461, pp. 217-236, 1999.

[12] A. Beopoulos, T. Chardot, and J. M. Nicaud, "*Yarrowia lipolytica*: A model and a tool to understand the mechanisms implicated in lipid accumulation," Biochimie, vol. 91, pp. 692-6, June 2009.

[13] G. Barth and C. Gaillardin, "Physiology and genetics of the dimorphic fungus *Yarrowia lipolytica*," FEMS Microbiology Reviews, vol. 19, pp. 219-237, 1997.

[14] S. Mauersberger, H. J. Wang, C. Gaillardin, G. Barth, and J. M. Nicaud, "Insertional Mutagenesis in the n-Alkane-Assimilating Yeast *Yarrowia lipolytica*: Generation of Tagged Mutations in Genes Involved in Hydrophobic Substrate Utilization," Journal of Bacteriology, vol. 183, pp. 5102-5109, 2001.

[15] F. Thevenieau, M. T. Le Dall, B. Nthangeni, S. Mauersberger, R. Marchal, and J. M. Nicaud, "Characterization of *Yarrowia lipolytica* mutants affected in hydrophobic substrate utilization," Fungal genetics and biology: FG & B, vol. 44, pp. 531-42, June 2007.

[16] F. Thevenieau, A. Beopoulos, T. Desfougeres, J. Sabirova, K. Albertin, S. Zinjarde, and J. M. Nicaud, "Uptake and Assimilation of Hydrophobic Substrates by the Oleaginous Yeast *Yarrowia lipolytica*," pp. 1513-1527, 2010.

[17] J. R. Borden and E. T. Papoutsakis, "Dynamics of genomic-library enrichment and identification of solvent tolerance genes for *Clostridium acetobutylicum*," Applied and Environmental Microbiology, vol. 73, pp. 3061-8, May 2007.

[18] M. J. Dunlop, Z. Y. Dossani, H. L. Szmidt, H. C. Chu, T. S. Lee, J. D. Keasling, M. Z. Hadi, and A. Mukhopadhyay, "Engineering microbial biofuel tolerance and export using efflux pumps," Molecular systems biology, vol. 7, p. 487, May 10, 2011.

[19] K. L. Heckman and L. R. Pease, "Gene splicing and mutagenesis by PCR-driven overlap extension," Nature protocols, vol. 2, pp. 924-32, 2007.

[20] M. A. Sheff and K. S. Thorn, "Optimized cassettes for fluorescent protein tagging in *Saccharomyces cerevisiae*," Yeast, vol. 21, pp. 661-70, June 2004.

[21] S. Blanchin-Roland, G. Da Costa, and C. Gaillardin, "ESCRT-I components of the endocytic machinery are required for Rim101-dependent ambient pH regulation in the yeast *Yarrowia lipolytica*," Microbiology, vol. 151, pp. 3627-37, November 2005.

[22] H. Riezmant, T. Hase, A. P. G. M. v. Loon, L. A. Grivell, K. Suda, and G. Schatz, "Import of proteins into mitochondria: a 70 kilodalton outer membrane protein with a large carboxy-terminal deletion is still transported to the outer membrane," The European Molecular Biology Organization Journal, vol. 2, pp. 2161-2168, 1983.

[23] A. Conzelmann, H. Riezman, C. Desponds, and C. Bron, "A major 125-kd membrane glycoprotein of *Saccharomyces cerevisiae* is attached to the lipid bilayer through an inositol-containing phospholipid," the The European Molecular Biology Organization Journal vol. 7, pp. 2233-2240, July 1988.

The invention claimed is:

1. A recombinant *Saccharomyces cerevisiae* cell expressing a heterologous ATP binding cassette 2 (ABC2) polypeptide having the amino acid sequence set forth in SEQ ID NO:4, wherein the ABC2 polypeptide is capable of exporting C10-C11 alkanes.

2. The recombinant *Saccharomyces cerevisiae* cell of claim 1, wherein the cell comprises a plasmid comprising a nucleic acid molecule encoding the heterologous ABC2 polypeptide.

3. A method for the production of a C6-C16 alkane comprising culturing the recombinant *Saccharomyces cerevisiae* cell of claim 1 under conditions that allow (i) the expression of the heterologous ABC2 polypeptide; and (ii) the production of a C6-C16 alkane.

4. A method of increasing resistance of toxicity to C10-C11 alkanes in a *Saccharomyces cerevisiae* cell comprising:
   a. transforming a *Saccharomyces cerevisiae* cell with a nucleic acid molecule encoding a heterologous ATP binding cassette 2 (ABC2) polypeptide having the amino acid sequence set forth in SEQ ID NO:4, wherein the ABC2 polypeptide is capable of exporting C10-C11 alkanes; and
   b. culturing said transformed *Saccharomyces cerevisiae* cell under conditions that allow expression of the heterologous ABC2 polypeptide.

5. The method of claim 4 wherein the nucleic acid molecule is within a plasmid.

6. The method of claim 4, wherein said transformed *Saccharomyces cerevisiae* cell is capable of producing a C6-C16 alkane.

7. The method of claim 6, wherein said transformed *Saccharomyces cerevisiae* cell is capable of producing a decane.

8. The method of claim 6, wherein said transformed *Saccharomyces cerevisiae* cell is capable of producing an undecane.

* * * * *

SEQUENCE LISTING

```
<160> NUMBER OF SEQ ID NOS: 9

<210> SEQ ID NO 1
<211> LENGTH: 240
<212> TYPE: PRT
<213> ORGANISM: Artificial Sequence
<220> FEATURE:
<223> OTHER INFORMATION: Nucleotide Binging Domain 2 (NBD2) ABC domain
      consensus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (96)..(97)
<223> OTHER INFORMATION: Xaa can be any naturally occurring amino acid
<220> FEATURE:
```

<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (167)..(168)
<223> OTHER INFORMATION: Xaa can be any naturally occurring amino acid
<220> FEATURE:
<221> NAME/KEY: misc_feature
<222> LOCATION: (175)..(176)
<223> OTHER INFORMATION: Xaa can be any naturally occurring amino acid
<220> FEATURE:
<221> NAME/KEY: MISC_FEATURE
<222> LOCATION: (188)..(188)
<223> OTHER INFORMATION: needed for alkane transport
<220> FEATURE:
<221> NAME/KEY: misc_feature
<222> LOCATION: (201)..(203)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (215)..(216)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (221)..(222)
<223> OTHER INFORMATION: Xaa can be any naturally occurring amino acid
<220> FEATURE:
<221> NAME/KEY: misc_feature
<222> LOCATION: (226)..(227)
<223> OTHER INFORMATION: Xaa can be any naturally occurring amino acid
<220> FEATURE:
<221> NAME/KEY: misc_feature
<222> LOCATION: (234)..(236)
<223> OTHER INFORMATION: Xaa can be any naturally occurring amino acid

<400> SEQUENCE: 1

Glu Xaa Arg Leu Leu Asp Xaa Val Asp Gly Xaa Val Lys Pro Gly Thr
1               5                   10                  15

Leu Thr Ala Leu Met Gly Xaa Ser Gly Ala Gly Lys Thr Thr Leu Leu
            20                  25                  30

Asp Val Leu Ala Asp Arg Lys Xaa Thr Gly Val Xaa Thr Gly Xaa Met
        35                  40                  45

Xaa Val Asn Gly Xaa Xaa Arg Asp Xaa Ser Phe Gln Arg Lys Thr Gly
    50                  55                  60

Tyr Val Gln Gln Gln Asp Leu His Thr Ala Thr Xaa Thr Val Arg Glu
65                  70                  75                  80

Xaa Leu Glu Phe Ser Ala Leu Leu Arg Gln Pro Ser Xaa Xaa Pro Xaa
                85                  90                  95

Xaa Glu Lys Xaa Ala Tyr Val Asp Glu Val Ile Xaa Ile Leu Glu Met
            100                 105                 110

Xaa Xaa Tyr Ala Asp Ala Val Val Gly Val Pro Gly Glu Gly Leu Asn
        115                 120                 125

Val Glu Gln Arg Lys Arg Leu Thr Ile Gly Val Glu Leu Ala Ala Lys

```
                130                 135                 140
Pro Glu Leu Leu Leu Phe Leu Asp Glu Pro Thr Ser Gly Leu Asp Ser
145                 150                 155                 160

Gln Thr Ala Trp Ser Ile Xaa Xaa Leu Leu Lys Lys Leu Ala Xaa Xaa
                165                 170                 175

Gly Gln Ala Ile Leu Cys Thr Ile His Gln Pro Ser Ala Ile Leu Phe
                180                 185                 190

Gln Glu Phe Asp Arg Leu Leu Phe Xaa Xaa Xaa Gly Gly Xaa Thr Val
                195                 200                 205

Tyr Tyr Gly Asp Ile Gly Xaa Xaa Ser Ser Xaa Leu Xaa Xaa Tyr Phe
                210                 215                 220

Glu Xaa Xaa Gly Ala Asp Pro Cys Pro Xaa Xaa Xaa Asn Pro Ala Glu
225                 230                 235                 240

<210> SEQ ID NO 2
<211> LENGTH: 240
<212> TYPE: PRT
<213> ORGANISM: Yarrowia lipolytica
<220> FEATURE:
<221> NAME/KEY: MISC_FEATURE
<222> LOCATION: (188)..(188)
<223> OTHER INFORMATION: needed for alkane transporter activity

<400> SEQUENCE: 2

Glu Arg Arg Leu Leu Asp His Val Asp Gly Phe Val Lys Pro Gly Thr
1               5                   10                  15

Leu Thr Ala Leu Met Gly Ala Ser Gly Ala Gly Lys Thr Thr Leu Leu
                20                  25                  30

Asp Val Leu Ala Asp Arg Lys Ser Thr Gly Val Val Thr Gly Glu Met
                35                  40                  45

Leu Val Asn Gly Glu His Arg Asp Gly Ser Phe Gln Arg Lys Thr Gly
                50                  55                  60

Tyr Val Gln Gln Gln Asp Leu His Thr Ala Thr Ala Thr Val Arg Glu
65                  70                  75                  80

Ser Leu Glu Phe Ser Ala Leu Leu Arg Gln Pro Ser Ser Ile Pro Glu
                85                  90                  95

Ser Glu Lys Leu Ala Tyr Val Asp Glu Val Ile Arg Ile Leu Glu Met
                100                 105                 110

Glu Thr Tyr Ala Asp Ala Val Val Gly Val Pro Gly Glu Gly Leu Asn
                115                 120                 125

Val Glu Gln Arg Lys Arg Leu Thr Ile Gly Val Glu Leu Ala Ala Lys
                130                 135                 140

Pro Glu Leu Leu Leu Phe Leu Asp Glu Pro Thr Ser Gly Leu Asp Ser
145                 150                 155                 160

Gln Thr Ala Trp Ser Ile Val Lys Leu Leu Lys Lys Leu Ala Ala Asn
                165                 170                 175

Gly Gln Ala Ile Leu Cys Thr Ile His Gln Pro Ser Ala Ile Leu Phe
                180                 185                 190

Gln Glu Phe Asp Arg Leu Leu Phe Leu Ala Ser Gly Gly Arg Thr Val
                195                 200                 205

Tyr Tyr Gly Asp Ile Gly Pro Gln Ser Ser Ile Leu Thr Glu Tyr Phe
                210                 215                 220

Glu Arg Asn Gly Ala Asp Pro Cys Pro Lys Gln Gly Asn Pro Ala Glu
225                 230                 235                 240

<210> SEQ ID NO 3
```

```
<211> LENGTH: 240
<212> TYPE: PRT
<213> ORGANISM: Yarrowia lipolytica
<220> FEATURE:
<221> NAME/KEY: MISC_FEATURE
<222> LOCATION: (188)..(188)
<223> OTHER INFORMATION: needed for alkane transporter activity

<400> SEQUENCE: 3
```

| Glu | Lys | Arg | Leu | Leu | Asp | Asn | Val | Asp | Gly | Trp | Val | Lys | Pro | Gly | Thr |
|---|---|---|---|---|---|---|---|---|---|---|---|---|---|---|---|
| 1 | | | | 5 | | | | | 10 | | | | | 15 | |

| Leu | Thr | Ala | Leu | Met | Gly | Cys | Ser | Gly | Ala | Gly | Lys | Thr | Thr | Leu | Leu |
|---|---|---|---|---|---|---|---|---|---|---|---|---|---|---|---|
| | | | 20 | | | | 25 | | | | | 30 | | | |

| Asp | Val | Leu | Ala | Asp | Arg | Lys | Ala | Thr | Gly | Val | Ile | Thr | Gly | Asp | Met |
|---|---|---|---|---|---|---|---|---|---|---|---|---|---|---|---|
| | | 35 | | | | | 40 | | | | | | 45 | | |

| Arg | Val | Asn | Gly | Gln | Lys | Arg | Asp | Ala | Ser | Phe | Gln | Arg | Lys | Thr | Gly |
|---|---|---|---|---|---|---|---|---|---|---|---|---|---|---|---|
| 50 | | | | | 55 | | | | | 60 | | | | | |

| Tyr | Val | Gln | Gln | Gln | Asp | Leu | His | Thr | Ala | Thr | Ser | Thr | Val | Arg | Glu |
|---|---|---|---|---|---|---|---|---|---|---|---|---|---|---|---|
| 65 | | | | | 70 | | | | | 75 | | | | | 80 |

| Ala | Leu | Glu | Phe | Ser | Ala | Leu | Leu | Arg | Gln | Pro | Ser | Asn | Val | Pro | Lys |
|---|---|---|---|---|---|---|---|---|---|---|---|---|---|---|---|
| | | | | 85 | | | | | 90 | | | | | 95 | |

| Ala | Glu | Lys | Ile | Ala | Tyr | Val | Asp | Glu | Val | Ile | Asp | Ile | Leu | Glu | Met |
|---|---|---|---|---|---|---|---|---|---|---|---|---|---|---|---|
| | | | 100 | | | | | 105 | | | | | 110 | | |

| Gln | Ala | Tyr | Ala | Asp | Ala | Val | Val | Gly | Val | Pro | Gly | Glu | Gly | Leu | Asn |
|---|---|---|---|---|---|---|---|---|---|---|---|---|---|---|---|
| | | | 115 | | | | | 120 | | | | | 125 | | |

| Val | Glu | Gln | Arg | Lys | Arg | Leu | Thr | Ile | Gly | Val | Glu | Leu | Ala | Ala | Lys |
|---|---|---|---|---|---|---|---|---|---|---|---|---|---|---|---|
| 130 | | | | | 135 | | | | | 140 | | | | | |

| Pro | Glu | Leu | Leu | Leu | Phe | Leu | Asp | Glu | Pro | Thr | Ser | Gly | Leu | Asp | Ser |
|---|---|---|---|---|---|---|---|---|---|---|---|---|---|---|---|
| 145 | | | | | 150 | | | | | 155 | | | | | 160 |

| Gln | Thr | Ala | Trp | Ser | Ile | Ile | Cys | Leu | Leu | Lys | Lys | Leu | Ala | Asn | Arg |
|---|---|---|---|---|---|---|---|---|---|---|---|---|---|---|---|
| | | | | 165 | | | | | 170 | | | | | 175 | |

| Gly | Gln | Ala | Ile | Leu | Cys | Thr | Ile | His | Gln | Pro | Ser | Ala | Ile | Leu | Phe |
|---|---|---|---|---|---|---|---|---|---|---|---|---|---|---|---|
| | | | 180 | | | | | 185 | | | | | 190 | | |

| Gln | Glu | Phe | Asp | Arg | Leu | Leu | Phe | Met | Thr | Leu | Gly | Gly | Lys | Thr | Val |
|---|---|---|---|---|---|---|---|---|---|---|---|---|---|---|---|
| | | | 195 | | | | | 200 | | | | | 205 | | |

| Tyr | Tyr | Gly | Asp | Ile | Gly | Ala | Asn | Ser | Ser | Ala | Leu | Ile | Asn | Tyr | Phe |
|---|---|---|---|---|---|---|---|---|---|---|---|---|---|---|---|
| | | | 210 | | | | | 215 | | | | | 220 | | |

| Glu | Ser | Lys | Gly | Ala | Asp | Pro | Cys | Pro | Glu | Glu | Ala | Asn | Pro | Ala | Glu |
|---|---|---|---|---|---|---|---|---|---|---|---|---|---|---|---|
| 225 | | | | | 230 | | | | | 235 | | | | | 240 |

```
<210> SEQ ID NO 4
<211> LENGTH: 1469
<212> TYPE: PRT
<213> ORGANISM: Yarrowia lipolytica

<400> SEQUENCE: 4
```

| Met | Glu | Gln | Thr | Pro | Pro | Asp | Tyr | Thr | Gly | Leu | Asp | Lys | Asn | Ile | Asp |
|---|---|---|---|---|---|---|---|---|---|---|---|---|---|---|---|
| 1 | | | | 5 | | | | | 10 | | | | | 15 | |

| Ala | Glu | Val | Arg | Ser | Ile | Ala | Glu | Ser | Met | Tyr | Gln | Thr | Arg | Arg | Glu |
|---|---|---|---|---|---|---|---|---|---|---|---|---|---|---|---|
| | | | 20 | | | | | 25 | | | | | 30 | | |

| Gly | Val | Asn | Asp | Ser | Asp | Thr | Asp | Glu | Glu | Leu | Gln | Arg | Thr | Asn | Thr |
|---|---|---|---|---|---|---|---|---|---|---|---|---|---|---|---|
| | | | 35 | | | | | 40 | | | | | 45 | | |

| Ile | Gln | Pro | Asn | Leu | Asn | Val | Asn | Pro | Phe | Leu | Asp | Thr | Ser | Asp | Pro |
|---|---|---|---|---|---|---|---|---|---|---|---|---|---|---|---|
| | 50 | | | | | 55 | | | | | 60 | | | | |

| Gln | Leu | Asp | Pro | Leu | Ser | Lys | Glu | Phe | Asn | Ser | Arg | Lys | Trp | Ile | Lys |
|---|---|---|---|---|---|---|---|---|---|---|---|---|---|---|---|
| 65 | | | | | 70 | | | | | 75 | | | | | 80 |

| Thr | Ile | Leu | Gly | Leu | Lys | Ala | Arg | Phe | Gly | Asn | Ser | Arg | Ser | Ile | Ser |
|---|---|---|---|---|---|---|---|---|---|---|---|---|---|---|---|

```
            85                  90                  95
Ala Gly Val Ser Phe Lys Asn Leu Ser Ala Phe Gly Tyr Gly Gly
            100                 105                 110

Asn Asp Tyr Gln Lys Thr Phe Thr Asn Ser Val Met Ala Ile Gly Pro
            115                 120                 125

Met Ile Lys Lys Val Leu Gly Gly Asn Lys Gly Ser Glu Val Gln Ile
130                 135                 140

Leu Arg His Phe Asp Gly Leu Arg Ala Gly Glu Thr Cys Val Val
145                 150                 155                 160

Leu Gly Arg Pro Gly Ser Gly Cys Thr Thr Phe Leu Lys Ser Val Ala
            165                 170                 175

Cys Glu Thr Tyr Gly Phe His Leu Gly Glu Lys Ser Glu Trp Asn Tyr
            180                 185                 190

Gln Gly Val Pro Arg Asp Val Met Gln Lys Asn Ala Arg Gly Glu Ile
            195                 200                 205

Val Tyr Asn Ala Glu Val Asp Val His Phe Pro His Leu Thr Val Gly
            210                 215                 220

Asp Thr Leu Leu Phe Ala Ala Leu Ala Arg Thr Pro Gln Asn Arg Leu
225                 230                 235                 240

Glu Gly Val Ser Arg Glu Gln His Ala Thr His Val Arg Asp Val Ser
            245                 250                 255

Met Ala Met Leu Gly Leu Thr His Thr Met Asp Thr Lys Val Gly Asn
            260                 265                 270

Asp Phe Val Arg Gly Val Ser Gly Gly Glu Arg Lys Arg Val Ser Ile
            275                 280                 285

Ala Glu Ser Val Val Cys Gly Ala Pro Leu Gln Cys Trp Asp Asn Ser
            290                 295                 300

Thr Arg Gly Leu Asp Ala Ala Asn Ala Thr Glu Phe Ile Arg Ser Leu
305                 310                 315                 320

Arg Leu Ser Ala Glu Met Thr Asp Ala Ser Met Phe Val Ser Leu Tyr
            325                 330                 335

Gln Ala Ser Gln Glu Ala Tyr Asp Met Phe Asp Lys Val Cys Val Leu
            340                 345                 350

Tyr Glu Gly Arg Gln Ile Tyr Phe Gly Lys Thr Thr Glu Ala Lys Gln
            355                 360                 365

Phe Phe Leu Asp Leu Gly Phe Asp Cys Ala Asp Arg Gln Thr Thr Gly
            370                 375                 380

Asp Phe Leu Thr Ser Leu Thr Asn Pro Ile Glu Arg Ile Arg Pro
385                 390                 395                 400

Gly Trp Glu Ser Arg Val Pro Arg Thr Pro Asp Asp Phe Glu Lys Cys
            405                 410                 415

Trp Leu Glu Ser Glu Ala Arg Gln Leu Leu Gln Asp Ile Asp Glu
            420                 425                 430

Phe Asn Asn Glu Phe Val Leu Gly Gly Pro Ala Leu Asp Asn Phe Met
            435                 440                 445

Gly Leu Arg Lys Asp Ala Gln Ala Lys His Thr Arg Val Gln Ser Pro
            450                 455                 460

Tyr Thr Ile Ser Trp Pro Met Gln Thr Arg Leu Cys Leu Trp Arg Gly
465                 470                 475                 480

Phe Leu Arg Ile Lys Gly Asp Met Ser Thr Asp Ile Ala Thr Val Phe
            485                 490                 495

Gly Asn Phe Val Met Ala Leu Val Leu Ser Ser Met Phe Tyr Asn Met
            500                 505                 510
```

-continued

```
Pro Gln Thr Thr Glu Ser Phe Phe Ser Arg Gly Ala Leu Leu Phe Phe
                515                 520                 525

Ala Ile Leu Ile Asn Ala Phe Ala Ser Ile Leu Glu Ile Leu Ser Leu
            530                 535                 540

Tyr Glu Gln Arg Pro Ile Val Asp Lys Gln Asn Arg Tyr Ala Met Tyr
545                 550                 555                 560

His Pro Ala Ala Asp Ala Leu Ala Ala Ile Ile Thr Thr Phe Pro Thr
                565                 570                 575

Lys Thr Leu Thr Leu Val Ser Val Asn Leu Thr Ile Tyr Phe Met Thr
                580                 585                 590

Asn Leu Arg Arg Glu Val Gly Pro Phe Ile Phe Leu Phe Ser
            595                 600                 605

Leu Leu Cys Thr Met Ala Met Ser Met Ile Phe Arg Thr Ile Gly Ser
            610                 615                 620

Val Thr Lys Thr Leu Glu Gln Ala Leu Ala Pro Ala Ser Ile Ile Ile
625                 630                 635                 640

Leu Ala Leu Val Ile Tyr Thr Gly Phe Ser Leu Pro Ile Ser Tyr Met
                645                 650                 655

His Gly Trp Ala Arg Trp Ile Asn Trp Leu Asn Pro Val Ala Tyr Gly
                660                 665                 670

Phe Glu Ala Val Met Val Asn Glu Phe Arg Asn Arg Glu Tyr Glu Cys
                675                 680                 685

Ser Met Phe Val Pro Ser Gly Gly Ala Tyr Glu Asn Val Ser Leu Asp
                690                 695                 700

Tyr Arg Ser Cys Ala Ala Val Gly Ala Glu Pro Gly Leu Arg Phe Val
705                 710                 715                 720

Asn Gly Asp Ala Phe Ile Asn Gln Ser Tyr Glu Tyr Tyr Asn Ala His
                725                 730                 735

Leu Trp Arg Asn Met Gly Ile Leu Phe Gly Phe Ile Ile Phe Phe Gly
                740                 745                 750

Ala Phe Tyr Leu Phe Ala Val Glu Tyr Ile Gln Gly Ala Lys Ser Lys
                755                 760                 765

Gly Glu Val Leu Val Phe Arg Lys Glu His Ile Lys Lys Gln Arg Lys
                770                 775                 780

Glu Lys Asn Gly Asp Ile Glu Ser Gly Val Thr Met Ala Gly Glu Lys
785                 790                 795                 800

Gly Thr Gln Glu Ser Glu Ser Ser Asn Thr Ser Ile Asn Leu Gln Ala
                805                 810                 815

Gln Arg Gly Ile Tyr Gln Trp Lys Asp Val Cys Tyr Asp Ile Lys Val
                820                 825                 830

Lys Asp Gly Glu Arg Arg Leu Leu Asp His Val Asp Gly Phe Val Lys
                835                 840                 845

Pro Gly Thr Leu Thr Ala Leu Met Gly Ala Ser Gly Ala Gly Lys Thr
850                 855                 860

Thr Leu Leu Asp Val Leu Ala Asp Arg Lys Ser Thr Gly Val Val Thr
865                 870                 875                 880

Gly Glu Met Leu Val Asn Gly Glu His Arg Asp Gly Ser Phe Gln Arg
                885                 890                 895

Lys Thr Gly Tyr Val Gln Gln Asp Leu His Thr Ala Thr Ala Thr
                900                 905                 910

Val Arg Glu Ser Leu Glu Phe Ser Ala Leu Leu Arg Gln Pro Ser Ser
                915                 920                 925
```

```
Ile Pro Glu Ser Glu Lys Leu Ala Tyr Val Asp Glu Val Ile Arg Ile
    930                 935                 940

Leu Glu Met Glu Thr Tyr Ala Asp Ala Val Val Gly Val Pro Gly Glu
945                 950                 955                 960

Gly Leu Asn Val Glu Gln Arg Lys Arg Leu Thr Ile Gly Val Glu Leu
                965                 970                 975

Ala Ala Lys Pro Glu Leu Leu Leu Phe Leu Asp Glu Pro Thr Ser Gly
            980                 985                 990

Leu Asp Ser Gln Thr Ala Trp Ser Ile Val Lys Leu Leu Lys Lys Leu
        995                 1000                1005

Ala Ala Asn Gly Gln Ala Ile Leu Cys Thr Ile His Gln Pro Ser
    1010                1015                1020

Ala Ile Leu Phe Gln Glu Phe Asp Arg Leu Leu Phe Leu Ala Ser
    1025                1030                1035

Gly Gly Arg Thr Val Tyr Tyr Gly Asp Ile Gly Pro Gln Ser Ser
    1040                1045                1050

Ile Leu Thr Glu Tyr Phe Glu Arg Asn Gly Ala Asp Pro Cys Pro
    1055                1060                1065

Lys Gln Gly Asn Pro Ala Glu Trp Met Leu Glu Val Ile Gly Ala
    1070                1075                1080

Ala Pro Gly Ser Thr Ala Lys Arg Asp Trp Pro Val Val Trp Ala
    1085                1090                1095

Glu Ser Pro Glu Arg Ala Ala Lys Arg Glu Glu Leu Asp Glu Met
    1100                1105                1110

Ala Arg Thr Val Glu Arg Val Gln Thr Asn Thr Thr Glu Arg Asp
    1115                1120                1125

Ser Thr Gly Tyr Ser Asp Ser Asp Gln Phe Ala Val Gly Trp Trp
    1130                1135                1140

Thr Gln Phe Lys Ile Val Ser Lys Arg Gln Phe Gln Ala Leu Trp
    1145                1150                1155

Arg Thr Pro Ser Tyr Leu Trp Ser Lys Val Phe Leu Cys Ala Ala
    1160                1165                1170

Ser Ala Ile Phe Ile Gly Phe Ser Phe Phe Lys Ala Pro Asn Asp
    1175                1180                1185

Met Gln Gly Leu Gln Asn Lys Met Phe Ser Phe Met Leu Phe
    1190                1195                1200

Leu Ile Phe Asn Thr Val Val Glu Gln Ile Ile Pro Gln Phe Asp
    1205                1210                1215

Lys Met Arg Glu Leu Tyr Glu Ala Arg Glu Arg Ser Ser Lys Thr
    1220                1225                1230

Tyr Ser Trp Gln Val Phe Met Gly Ser Asn Met Val Val Glu Leu
    1235                1240                1245

Ile Trp Gln Phe Phe Met Gly Val Ile Val Phe Cys Phe Tyr
    1250                1255                1260

Tyr Pro Val Gly Phe Gln Trp Thr Ala Gly Tyr Asn Asp Ser Val
    1265                1270                1275

His Glu Arg Gly Gly Leu Phe Phe Leu Tyr Val Leu Leu Leu Phe
    1280                1285                1290

Leu Tyr Asn Ser Thr Phe Ala His Met Leu Ile Ala Gly Ile Asp
    1295                1300                1305

Asn Lys Asp Thr Ala Ala Gln Ile Gly Thr Leu Leu Phe Thr Leu
    1310                1315                1320

Met Leu Leu Phe Cys Gly Val Leu Ala Thr Lys Glu Gln Met Pro
```

```
                1325                1330                1335
Gly Phe Trp Val Phe Met Tyr Arg Val Ser Pro Leu Thr Tyr Phe
    1340                1345                1350
Val Gly Gly Met Met Ala Thr Gly Met Gly Arg Ala Pro Val Thr
    1355                1360                1365
Cys Ser Pro His Glu Leu Val Arg Phe Pro Ala Val Pro Gly Lys
    1370                1375                1380
Ser Cys Gly Glu Tyr Met Asp Gly Phe Ile Ser Ala Leu Gly Asp
    1385                1390                1395
Ser Ala Gly Tyr Leu Val Ser Ser Ser Ala Asp Met Cys Glu Tyr
    1400                1405                1410
Cys Pro Met Lys Ser Ser Asp Gln Phe Leu Asp Ser Val Asp Ile
    1415                1420                1425
Ser Tyr Thr Gln Arg Trp Arg Asn Trp Gly Ile Leu Trp Ala Tyr
    1430                1435                1440
Pro Leu Phe Asn Ile Phe Ala Ala Phe Ala Leu Tyr Tyr Phe Phe
    1445                1450                1455
Arg Val Pro Lys Lys Ser Lys Ala Gln Lys Ala
    1460                1465

<210> SEQ ID NO 5
<211> LENGTH: 1485
<212> TYPE: PRT
<213> ORGANISM: Yarrowia lipolytica

<400> SEQUENCE: 5

Met Thr Asp Pro Val Pro Ile Thr Gln Asp Pro Thr Ile Tyr Ser Ser
1               5                   10                  15
Gln Gln Asp Ala Glu Ile Arg Ser Leu Ala Glu Ser Ile His Ser Gln
                20                  25                  30
His Ser Asn Asn Ser Asn Asn Ser Thr Glu Leu Thr Asn Pro Tyr Val
            35                  40                  45
Asp Thr Ser Asp Pro Glu Leu Asp Pro Trp Ser Gly Gln Phe Asn Ser
        50                  55                  60
Arg Lys Trp Ser Arg Thr Ile Leu Gly Leu Lys Arg Arg Tyr Gly Thr
65                  70                  75                  80
Ser Lys Glu Ile Thr Ala Gly Val Ser Phe Lys Asn Leu Gly Ala Tyr
                85                  90                  95
Gly Tyr Gly Gly Gly Ala Asp Tyr Gln Lys Thr Val Ala Asn Ala Val
                100                 105                 110
Leu Gly Leu Glu Gly Val Val Arg Thr Leu Phe His Leu Glu Lys Lys
            115                 120                 125
Glu Asp Lys Val Gln Ile Leu Ser Asp Phe Asn Gly Val Leu Trp Pro
        130                 135                 140
Gly Glu Thr Cys Val Val Leu Gly Arg Pro Gly Ser Gly Cys Thr Thr
145                 150                 155                 160
Leu Leu Lys Ser Ile Ala Cys Glu Thr Tyr Gly Phe Gln Leu Asp Lys
                165                 170                 175
Glu Thr Glu Trp Asn Tyr Gln Gly Ile Pro Arg Lys Ile Met Gln Lys
                180                 185                 190
Thr Cys Arg Gly Glu Ile Val Tyr Asn Ala Glu Val Asp Val His Phe
            195                 200                 205
Pro His Leu Thr Val Gly Asp Thr Leu Met Phe Ala Ser Leu Ala Arg
        210                 215                 220
```

-continued

| | | | | | | | | | | | | | | |
|---|---|---|---|---|---|---|---|---|---|---|---|---|---|---|
|Thr|Pro|Gln|Asn|Arg|Phe|Asp|Gly|Val|Thr|Arg|Glu|Gln|Tyr|Ala|Lys|
|225| | | | |230| | | | |235| | | | |240|

His Thr Arg Asp Val Thr Met Ala Ser Leu Gly Leu Ser His Thr Leu
                    245                 250                 255

Asp Thr Lys Val Gly Asn Asp Phe Val Arg Gly Val Ser Gly Gly Glu
            260                 265                 270

Arg Lys Arg Val Ser Ile Ala Glu Ser Ile Val Cys Gly Ser Pro Leu
        275                 280                 285

Gln Cys Trp Asp Asn Ser Thr Arg Gly Leu Asp Ala Ala Thr Ala Thr
    290                 295                 300

Glu Phe Leu Arg Trp Leu Arg His Ser Ala Glu Leu Thr Gly Ala Ser
305                 310                 315                 320

Met Phe Val Ser Leu Tyr Gln Ala Ser Gln Glu Ala Tyr Glu Leu Phe
                325                 330                 335

Asp Lys Val Thr Val Leu Tyr Glu Gly Gln Gln Ile Tyr Phe Gly Pro
            340                 345                 350

Gly Glu Gln Ala Lys Gln Tyr Phe Glu Glu Met Gly Phe Glu Cys Pro
        355                 360                 365

His Arg Gln Thr Thr Gly Asp Phe Leu Thr Ser Ile Thr Ser Pro Ala
    370                 375                 380

Glu Arg Ile Val Ala Pro Gly Phe Glu Gly Lys Thr Pro Arg Thr Ala
385                 390                 395                 400

Ser Glu Phe Ala Glu Arg Trp Arg Gln Ser Gln Ala Tyr Ala Asn Leu
                405                 410                 415

Gln Glu Glu Ile Glu Arg Phe Asn Thr Glu Phe Pro Val Gly Gly Asn
            420                 425                 430

Arg Val Ala Asp Ile Met Glu Leu Lys Gln Glu Lys Gln Ser Asp His
        435                 440                 445

Ile Lys Val Ser Ser Pro Tyr Thr Ile Ser Ile Pro Met Gln Val Lys
    450                 455                 460

Leu Cys Leu Thr Arg Gly Phe Gln Arg Leu Arg Gly Asp Leu Ser Met
465                 470                 475                 480

Ala Leu Thr Thr Val Leu Gly Asn Phe Val Val Ala Leu Ile Leu Ser
                485                 490                 495

Ser Met Phe Tyr Asn Met Pro Glu Asp Thr Ser Ser Phe Phe Ser Arg
            500                 505                 510

Gly Ala Leu Leu Phe Phe Ala Met Leu Met Asn Ala Met Ser Ser Val
        515                 520                 525

Leu Glu Ile Ile Val Leu Tyr Glu Leu Arg Pro Ile Val Glu Lys His
    530                 535                 540

Gln Arg Tyr Ala Met Tyr His Pro Phe Cys Glu Ala Leu Ala Ser Ile
545                 550                 555                 560

Ile Cys Asp Phe Pro Thr Lys Phe Leu Thr Met Leu Cys Val Asn Val
                565                 570                 575

Thr Leu Tyr Phe Met Ser Asn Leu Arg Arg Glu Ala Gly Pro Phe Phe
            580                 585                 590

Ile Phe Phe Leu Phe Thr Leu Leu Cys Val Leu Ala Met Ser Met Ile
        595                 600                 605

Phe Arg Thr Ile Ala Ala Val Thr Lys Thr Leu Gln Gln Ala Leu Ala
    610                 615                 620

Pro Ala Ala Val Ile Ile Leu Ala Leu Ile Ile Tyr Thr Gly Phe Thr
625                 630                 635                 640

Leu Pro Ile Ser Tyr Met Arg Gly Trp Ala Arg Trp Ile Asn Tyr Ile

-continued

```
                645                 650                 655
Asp Pro Ile Ala Tyr Gly Phe Glu Ala Val Met Val Asn Glu Phe Arg
            660                 665                 670

Asn Arg Glu Phe Pro Cys Ala Leu Phe Ile Pro Gln Gln Ser Thr Tyr
        675                 680                 685

Asp Gln Leu Gly Ser Pro Tyr Gln Gly Cys Met Ala Val Gly Ala Lys
    690                 695                 700

Pro Gly Glu Arg Phe Val Asn Gly Asp Arg Tyr Leu Glu Met Ala Phe
705                 710                 715                 720

Asp Tyr Ser Gln Ala His Leu Trp Arg Asn Leu Gly Ile Met Phe Gly
                725                 730                 735

Phe Ile Leu Phe Phe Ala Phe Thr Tyr Leu Thr Ala Val Glu Phe Ile
            740                 745                 750

Gln Ser Ala Lys Ser Lys Gly Glu Val Leu Val Phe Leu Arg Ser Ser
        755                 760                 765

Leu Lys Gln Arg Lys Lys Arg Ala His Leu Met Asp Val Glu Ala Asn
    770                 775                 780

Ala Glu Lys Val Gly Ala Ala Gln Asp Arg Glu Ile Leu Val Gln Gln
785                 790                 795                 800

Glu Glu Gly Gln Gln Glu Thr Ser Ser Cys Thr Pro Ser Asp Ser
                805                 810                 815

Thr Pro Lys Asp Ile Phe Gln Trp Lys Asp Val Cys Tyr Asp Ile Lys
            820                 825                 830

Val Lys Gly Gly Glu Lys Arg Leu Leu Asp Asn Val Asp Gly Trp Val
        835                 840                 845

Lys Pro Gly Thr Leu Thr Ala Leu Met Gly Cys Ser Gly Ala Gly Lys
    850                 855                 860

Thr Thr Leu Leu Asp Val Leu Ala Asp Arg Lys Ala Thr Gly Val Ile
865                 870                 875                 880

Thr Gly Asp Met Arg Val Asn Gly Gln Lys Arg Asp Ala Ser Phe Gln
                885                 890                 895

Arg Lys Thr Gly Tyr Val Gln Gln Gln Asp Leu His Thr Ala Thr Ser
            900                 905                 910

Thr Val Arg Glu Ala Leu Glu Phe Ser Ala Leu Leu Arg Gln Pro Ser
        915                 920                 925

Asn Val Pro Lys Ala Glu Lys Ile Ala Tyr Val Asp Glu Val Ile Asp
    930                 935                 940

Ile Leu Glu Met Gln Ala Tyr Ala Asp Ala Val Val Gly Val Pro Gly
945                 950                 955                 960

Glu Gly Leu Asn Val Glu Gln Arg Lys Arg Leu Thr Ile Gly Val Glu
                965                 970                 975

Leu Ala Ala Lys Pro Glu Leu Leu Leu Phe Leu Asp Glu Pro Thr Ser
            980                 985                 990

Gly Leu Asp Ser Gln Thr Ala Trp  Ser Ile Ile Cys Leu  Leu Lys Lys
        995                 1000                 1005

Leu Ala  Asn Arg Gly Gln Ala  Ile Leu Cys Thr Ile  His Gln Pro
    1010                 1015                 1020

Ser Ala  Ile Leu Phe Gln Glu  Phe Asp Arg Leu Leu  Phe Met Thr
    1025                 1030                 1035

Leu Gly  Gly Lys Thr Val Tyr  Tyr Gly Asp Ile Gly  Ala Asn Ser
    1040                 1045                 1050

Ser Ala  Leu Ile Asn Tyr Phe  Glu Ser Lys Gly Ala  Asp Pro Cys
    1055                 1060                 1065
```

-continued

Pro Glu Glu Ala Asn Pro Ala Glu Trp Met Leu Ala Ala Ile Gly
    1070                1075                1080

Ala Ala Pro Gly Ser Ile Ala Lys His Asp Trp Ala Val Val Trp
    1085                1090                1095

Asn Glu Ser Glu Glu Arg Ala Arg Glu Arg Asp Leu Leu Asp Lys
    1100                1105                1110

Met Ala Glu Glu Leu Ala Ala Gln Ser Thr His Asp Glu Lys Asn
    1115                1120                1125

Glu Leu Val Thr Ser Lys Ser Val Gly Ser Ser Gln Thr Ser Ser
    1130                1135                1140

Ser Ser Tyr Ser Ala Lys Ser Gln Tyr Ala Thr Ser Gln Ala Thr
    1145                1150                1155

Gln Leu Tyr Tyr Leu Thr Lys Arg Leu Trp Thr Tyr Tyr Trp Arg
    1160                1165                1170

Ser Pro Arg Tyr Ile Trp Ser Lys Leu Leu Met Ser Ile Ala Ser
    1175                1180                1185

Ala Leu Phe Ile Gly Phe Ser Tyr Tyr Lys Ala Ser Gln Asp Ile
    1190                1195                1200

Gln Gly Leu Gln Asn Gln Met Phe Ala Phe Phe Met Leu Phe Leu
    1205                1210                1215

Ile Phe Val Ile Ile Met Val Gln Ile Leu Pro His Phe Val Ala
    1220                1225                1230

Gln Arg Glu Leu Tyr Glu Ala Arg Glu Arg Ser Ser Met Ala Tyr
    1235                1240                1245

Ser Trp Gln Ala Phe Met Gly Ser Asn Ile Leu Val Glu Leu Pro
    1250                1255                1260

Trp Gln Thr Leu Val Ala Val Leu Val Phe Phe Cys Phe Tyr Tyr
    1265                1270                1275

Pro Ile Gly Leu Gln Asn Asn Ala Thr Gly His Leu Gly Glu Arg
    1280                1285                1290

Gly Ala Leu Phe Phe Leu Leu Leu Trp Ser Phe Tyr Val Tyr Asn
    1295                1300                1305

Ser Thr Phe Ala His Met Met Gly Ala Ala Phe Glu Asn Lys Glu
    1310                1315                1320

Asn Ala Ala Thr Ile Gly Tyr Leu Leu Phe Ala Leu Cys Leu Ile
    1325                1330                1335

Phe Cys Gly Val Leu Ala Thr Lys Glu Asp Met Pro His Phe Trp
    1340                1345                1350

Ile Phe Met Tyr Arg Val Ser Pro Leu Thr Tyr Leu Ile Ser Gly
    1355                1360                1365

Leu Leu Ser Ala Gly Val Gly Glu Thr Arg Val Glu Cys Thr Asp
    1370                1375                1380

Asn Glu Leu Val Leu Phe Lys Pro Met Asn Gly Thr Asn Cys Gly
    1385                1390                1395

Lys Tyr Met His Pro Phe Met Glu Gly Leu Gly His Thr Asp Met
    1400                1405                1410

Pro Met Gly Tyr Leu Val Asp Pro Ser Ala Thr Asp Met Cys Gly
    1415                1420                1425

Tyr Cys Pro Ile Ser Asn Thr Asn Gly Tyr Leu Asp Gln Ile Asp
    1430                1435                1440

Val Lys Tyr Ser Gln Arg Trp Arg Asn Tyr Gly Ile Leu Phe Ala
    1445                1450                1455

```
Tyr Pro Ala Phe Asn Val Phe Met Ala Phe Ala Phe Tyr Tyr Ile
    1460                1465            1470

Phe Arg Val Pro Lys Lys Ser Arg Lys Gln Lys Ala
    1475            1480            1485

<210> SEQ ID NO 6
<211> LENGTH: 240
<212> TYPE: PRT
<213> ORGANISM: Yarrowia lipolytica

<400> SEQUENCE: 6

Glu Arg Arg Leu Leu Asp His Val Asp Gly Phe Val Lys Pro Gly Thr
1               5                   10                  15

Leu Thr Ala Leu Met Gly Ala Ser Gly Ala Gly Lys Thr Thr Leu Leu
            20                  25                  30

Asp Val Leu Ala Asp Arg Lys Ser Thr Gly Val Val Thr Gly Glu Met
        35                  40                  45

Leu Val Asn Gly Glu His Arg Asp Gly Ser Phe Gln Arg Lys Thr Gly
    50                  55                  60

Tyr Val Gln Gln Gln Asp Leu His Thr Ala Thr Ala Thr Val Arg Glu
65                  70                  75                  80

Ser Leu Glu Phe Ser Ala Leu Leu Arg Gln Pro Ser Ser Ile Pro Glu
                85                  90                  95

Ser Glu Lys Leu Ala Tyr Val Asp Glu Val Ile Arg Ile Leu Glu Met
            100                 105                 110

Glu Thr Tyr Ala Asp Ala Val Val Gly Val Pro Gly Glu Gly Leu Asn
        115                 120                 125

Val Glu Gln Arg Lys Arg Leu Thr Ile Gly Val Glu Leu Ala Ala Lys
    130                 135                 140

Pro Glu Leu Leu Leu Phe Leu Asp Glu Pro Thr Ser Gly Leu Asp Ser
145                 150                 155                 160

Gln Thr Ala Trp Ser Ile Val Lys Leu Leu Lys Lys Leu Ala Ala Asn
                165                 170                 175

Gly Gln Ala Ile Leu Cys Thr Ile His Gln Pro Ser Ala Ile Leu Phe
            180                 185                 190

Gln Glu Phe Asp Arg Leu Leu Phe Leu Ala Ser Gly Gly Arg Thr Val
        195                 200                 205

Tyr Tyr Gly Asp Ile Gly Pro Gln Ser Ser Ile Leu Thr Glu Tyr Phe
    210                 215                 220

Glu Arg Asn Gly Ala Asp Pro Cys Pro Lys Gln Gly Asn Pro Ala Glu
225                 230                 235                 240

<210> SEQ ID NO 7
<211> LENGTH: 240
<212> TYPE: PRT
<213> ORGANISM: Yarrowia lipolytica

<400> SEQUENCE: 7

Glu Lys Arg Leu Leu Asp Asn Val Asp Gly Trp Val Lys Pro Gly Thr
1               5                   10                  15

Leu Thr Ala Leu Met Gly Cys Ser Gly Ala Gly Lys Thr Thr Leu Leu
            20                  25                  30

Asp Val Leu Ala Asp Arg Lys Ala Thr Gly Val Ile Thr Gly Asp Met
        35                  40                  45

Arg Val Asn Gly Gln Lys Arg Asp Ala Ser Phe Gln Arg Lys Thr Gly
    50                  55                  60
```

```
Tyr Val Gln Gln Gln Asp Leu His Thr Ala Thr Ser Thr Val Arg Glu
 65                  70                  75                  80

Ala Leu Glu Phe Ser Ala Leu Leu Arg Gln Pro Ser Asn Val Pro Lys
                 85                  90                  95

Ala Glu Lys Ile Ala Tyr Val Asp Val Ile Asp Ile Leu Glu Met
            100                 105                 110

Gln Ala Tyr Ala Asp Ala Val Val Gly Val Pro Gly Glu Gly Leu Asn
            115                 120                 125

Val Glu Gln Arg Lys Arg Leu Thr Ile Gly Val Glu Leu Ala Ala Lys
        130                 135                 140

Pro Glu Leu Leu Leu Phe Leu Asp Glu Pro Thr Ser Gly Leu Asp Ser
145                 150                 155                 160

Gln Thr Ala Trp Ser Ile Ile Cys Leu Leu Lys Lys Leu Ala Asn Arg
                165                 170                 175

Gly Gln Ala Ile Leu Cys Thr Ile His Gln Pro Ser Ala Ile Leu Phe
            180                 185                 190

Gln Glu Phe Asp Arg Leu Leu Phe Met Thr Leu Gly Gly Lys Thr Val
        195                 200                 205

Tyr Tyr Gly Asp Ile Gly Ala Asn Ser Ser Ala Leu Ile Asn Tyr Phe
210                 215                 220

Glu Ser Lys Gly Ala Asp Pro Cys Pro Glu Glu Ala Asn Pro Ala Glu
225                 230                 235                 240

<210> SEQ ID NO 8
<211> LENGTH: 240
<212> TYPE: PRT
<213> ORGANISM: Saccharomyces cerevisiae

<400> SEQUENCE: 8

Thr Arg Arg Ile Leu Asn Asn Val Asp Gly Trp Val Lys Pro Gly Thr
  1               5                  10                  15

Leu Thr Ala Leu Met Gly Ala Ser Gly Ala Gly Lys Thr Thr Leu Leu
             20                  25                  30

Asp Cys Leu Ala Glu Arg Val Thr Met Gly Val Ile Thr Gly Asp Ile
             35                  40                  45

Leu Val Asn Gly Ile Pro Arg Asp Lys Ser Phe Pro Arg Ser Ile Gly
         50                  55                  60

Tyr Cys Gln Gln Gln Asp Leu His Leu Lys Thr Ala Thr Val Arg Glu
 65                  70                  75                  80

Ser Leu Arg Phe Ser Ala Tyr Leu Arg Gln Pro Ala Glu Val Ser Ile
                 85                  90                  95

Glu Glu Lys Asn Arg Tyr Val Glu Glu Val Ile Lys Ile Leu Glu Met
            100                 105                 110

Glu Lys Tyr Ala Asp Ala Val Val Gly Val Ala Gly Glu Gly Leu Asn
            115                 120                 125

Val Glu Gln Arg Lys Arg Leu Thr Ile Gly Val Glu Leu Thr Ala Lys
        130                 135                 140

Pro Lys Leu Leu Val Phe Leu Asp Glu Pro Thr Ser Gly Leu Asp Ser
145                 150                 155                 160

Gln Thr Ala Trp Ser Ile Cys Gln Leu Met Lys Lys Leu Ala Asn His
                165                 170                 175

Gly Gln Ala Ile Leu Cys Thr Ile His Gln Pro Ser Ala Ile Leu Met
            180                 185                 190

Gln Glu Phe Asp Arg Leu Leu Phe Met Gln Arg Gly Gly Lys Thr Val
        195                 200                 205
```

```
Tyr Phe Gly Asp Leu Gly Glu Gly Cys Lys Thr Met Ile Asp Tyr Phe
        210                 215                 220

Glu Ser His Gly Ala His Lys Cys Pro Ala Asp Ala Asn Pro Ala Glu
225                 230                 235                 240

<210> SEQ ID NO 9
<211> LENGTH: 240
<212> TYPE: PRT
<213> ORGANISM: Saccharomyces cerevisiae

<400> SEQUENCE: 9

Gln Arg Arg Ile Leu Asn Asn Val Asp Gly Trp Val Lys Pro Gly Thr
1               5                   10                  15

Leu Thr Ala Leu Met Gly Ala Ser Gly Ala Gly Lys Thr Thr Leu Leu
            20                  25                  30

Asp Cys Leu Ala Glu Arg Val Thr Met Gly Val Ile Thr Gly Asn Ile
        35                  40                  45

Phe Val Asp Gly Arg Leu Arg Asp Glu Ser Phe Pro Arg Ser Ile Gly
    50                  55                  60

Tyr Cys Gln Gln Gln Asp Leu His Leu Lys Thr Ala Thr Val Arg Glu
65                  70                  75                  80

Ser Leu Arg Phe Ser Ala Tyr Leu Arg Gln Pro Ser Ser Val Ser Ile
            85                  90                  95

Glu Glu Lys Asn Arg Tyr Val Glu Glu Val Ile Lys Ile Leu Glu Met
            100                 105                 110

Gln Gln Tyr Ser Asp Ala Val Val Gly Val Ala Gly Glu Gly Leu Asn
            115                 120                 125

Val Glu Gln Arg Lys Arg Leu Thr Ile Gly Val Glu Leu Ala Ala Arg
    130                 135                 140

Pro Lys Leu Leu Val Phe Leu Asp Glu Pro Thr Ser Gly Leu Asp Ser
145                 150                 155                 160

Gln Thr Ala Trp Asp Thr Cys Gln Leu Met Arg Lys Leu Ala Thr His
                165                 170                 175

Gly Gln Ala Ile Leu Cys Thr Ile His Gln Pro Ser Ala Ile Leu Met
            180                 185                 190

Gln Gln Phe Asp Arg Leu Leu Phe Leu Gln Lys Gly Gly Gln Thr Val
        195                 200                 205

Tyr Phe Gly Asp Leu Gly Glu Gly Cys Lys Thr Met Ile Asp Tyr Phe
        210                 215                 220

Glu Ser Lys Gly Ala His Lys Cys Pro Pro Asp Ala Asn Pro Ala Glu
225                 230                 235                 240
```